(12) United States Patent
Fujita

(10) Patent No.: US 8,163,498 B2
(45) Date of Patent: Apr. 24, 2012

(54) METHOD FOR DETERMINATION OF MOLECULAR WEIGHT OF HYALURONIC ACID

(75) Inventor: Hiroshi Fujita, Higashiyamato (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 321 days.

(21) Appl. No.: 12/376,921

(22) PCT Filed: Aug. 8, 2007

(86) PCT No.: PCT/JP2007/065558
§ 371 (c)(1),
(2), (4) Date: Feb. 9, 2009

(87) PCT Pub. No.: WO2008/018519
PCT Pub. Date: Feb. 14, 2008

(65) Prior Publication Data
US 2010/0041071 A1 Feb. 18, 2010

(30) Foreign Application Priority Data
Aug. 8, 2006 (JP) .................................. 2006-215773

(51) Int. Cl.
*G01N 33/53* (2006.01)
(52) U.S. Cl. ........................... 435/7.1; 435/7.2; 436/518
(58) Field of Classification Search .................... None
See application file for complete search history.

(56) References Cited

U.S. PATENT DOCUMENTS
5,019,498 A  5/1991  Chichibu

FOREIGN PATENT DOCUMENTS
| EP | 0 283 779 | 9/1988 |
| JP | 09-229930 | 9/1997 |
| JP | 2000-065837 | 3/2000 |
| WO | WO 2005/001469 | 1/2005 |

OTHER PUBLICATIONS

Deb et al. J Biol Chem 1996 vol. 271, p. 2206-2212.*
International Search Report dated Aug. 30, 2007.
International Preliminary Report on Patentability and Written Opinion issued to PCT/JP2007/065558.
Fosang, et al. "An Elisa Plate Based Assay for Hyaluronan using Biotinylated Proteoglycan G1 Domain (HA-Binding Region)," *Matrix*, vol. 10, No. 5, pp. 306-313, Jan. 1990.
Pogrel, et al. "Hyaluronan (Hyaluronic Acid) and its Regulation in Human Saliva by Hyaluronidase and its Inhibitors," *Journal of Oral Science*, vol. 45, No. 2, pp. 85-91, Jun. 2003.
Supplementary European Search Report issued Sep. 3, 2009 to a related European application.

* cited by examiner

*Primary Examiner* — Jacob Cheu
(74) *Attorney, Agent, or Firm* — Knobbe, Martens, Olson & Bear, LLP

(57) ABSTRACT

A method of measuring a molecular weight of hyaluronic acid, comprising at least reacting hyaluronic acid in a sample containing the hyaluronic acid with a hyaluronic acid-binding protein to measure an amount of the hyaluronic acid-binding protein that is bound to the hyaluronic acid in the sample or a value that reflects the amount.

13 Claims, 15 Drawing Sheets

METHOD FOR DETERMINATION OF MOLECULAR WEIGHT OF HYALURONIC ACID

CROSS-REFERENCE TO RELATED APPLICATIONS

This application is the U.S. National Phase under 35 U.S.C. §371 of International Application PCT/JP2007/065558, filed Aug. 8, 2007, which was published in a non-English language, which claims priority to Japanese Patent Application No. 2006-215773, filed Aug. 8, 2006.

TECHNICAL FIELD

The present invention relates to a method of measuring a molecular weight of hyaluronic acid. More specifically, the present invention relates to a method in which the molecular weight of hyaluronic acid in a small amount of sample can be measured for a number of samples in a short time.

BACKGROUND ART

Meanings of the abbreviations used in the present description are as follows.
HA: Hyaluronic acid
BSA: Bovine serum albumin
CS-C: Chondroitin sulfate C
HA-BSA: HA-BSA conjugate
HABP: HA-binding protein
Biotin-HABP: Biotin labeled hyaluronic acid-binding protein
HRP-avidin: Horse-radish peroxidase labeled streptoavidin
OPD tablet: o-phenylenediamine tablet
ABTS tablet: 2,2'-azinobis(3-ethylbenzothiazoline-6-O-sulfonate)
TMB (+): N, N, N, N-tetramethylbenzidine (+)
TMB BLUE: N, N, N, N-tetramethylbenzidine blue
PBS: Salt-added sodium phosphate buffered saline
GPC: Gel permeation chromatography
SDS: Sodium dodecyl sulfate
TCA: Trichloroacetic acid
EDTA: Ethylenediamine tetraacetate
EGTA: Ethylene glycol-bis(2-aminoethylether)-N, N, N',N'-tetraacetic acid
TLCK: Nα-p-Tosyl-lysine chloromethyl ketone
TPCK: N-p-Tosyl-phenylalanine chloromethyl ketone HA is a naturally-occurring unbranched polysaccharide composed of repeating glucuronic acid and N-acetyl glucosamine disaccharide units. It has recently been pointed out, for example, that HA molecules which have different molecular weights show different bioactivities and that the molecular weight of HA of biological samples may be changed in some of the diseases. Accordingly, the method of measuring the molecular weight of HA is important in the fields of pharmaceuticals, medical care, and so on.

The measurement of the molecular weight of HA has generally been performed with a limiting viscosity measurement and a method utilizing GPC. The former is based on the principle that HA with higher molecular weight shows higher viscosity, and the latter is based on the principle of the size-exclusion chromatography in which HA with higher molecular weight migrate through the column more rapidly.

However, the limiting viscosity method requires about 1 mg or more of HA in order to carry out the measurement. Further, even if the general automatic devices is used, the maximum number of samples that can be measured simultaneously is 5 or less, and it required time-consuming manipulation such as drying of a viscosity tube for each measurement cycle. In addition, HA-specific measurement can not be achieved if other glycosaminoglycans coexist, because they exhibit similar viscosities. Further, coexisting substances other than the glycosaminoglycans also affect a solution viscosity. And finally, the measurement can not be performed unless an aqueous solution of the purified samples.

Further, the GPC method requires about 10 μg or more of HA in order to carry out the measurement. Further, it required at least 1 hour to equilibrate the measurement system, and it also required the measurement of a series of the molecular weight standards for each analysis. Not less than 5 different standards are generally used and need to be measured per one analytical batch in principle. In addition, the time required for one measurement cycle is at least 30 minutes. So it required 4 hours or more for only 1 test sample and 9 hours or more for 10 samples. And the GPC of the HA, UV detection is most sensitive currently, however, it also detect other glycosaminoglycans. Therefore, if other glycosaminoglycans coexist, the chromatogram of the glycosaminoglycans overlaps the chromatogram of HA, and HA-specific measurement can not be achieved. Similarly, if other contaminants which have some UV absorption coexist, HA-specific measurement can not be achieved. In many biological samples, there exist proteins, nucleic acids, lipids. which are having a double bond, and exhibits ultra violet absorption. Thus, in the case where the method is used to measure HA in biological samples, It required some pretreatment for removal of those contaminants.

As described above, the methods of measuring a molecular weight of HA that has been used up to the present requires at least about 10 μg to 1 mg of samples, much time, and complex manipulations, and besides the number of samples that can be measured simultaneously is restricted.

On the other hand, there have been proposed methods for the measurement of HA utilizing a protein binding to HA (Patent Documents 1 and 2), both of which are methods for quantitative measurement. There has not been known a method for direct measurement of a molecular weight at all.

Patent Document 1: JP 06-41952 B
Patent Document 2: JP 2698563 B

DISCLOSURE OF THE INVENTION

Problem to be Solved by the Invention

An object of the present invention is to provide a method of measuring a molecular weight of HA, in which the molecular weight of HA in a small amount of sample can be measured for a number of samples in a short time, and the molecular weight of HA can be measured even in the sample with which similar substances and other contaminants coexist.

Means for Solving the Problems

The inventors of the present invention have intensively studied in order to solve the above problems. As a result, the inventor has found that the reactivity of a protein binding to HA (HA-binding protein (HABP)) with HA may vary in a given direction in proportion to the molecular weight of HA, and confirmed that the finding can be utilized for the measurement of the molecular weight of HA, to thereby complete the present invention.

That is, the present invention provides a method of measuring a molecular weight of HA, including at least the reacting HA in a sample with a HABA to measure an amount of the HABP that is bound to the HA in the sample or a value that reflects the amount.

The reactivity of HABP with HA as described above varies in a given direction depending on the molecular weight of HA, and hence the molecular weight of HA causes change in an amount of HABP binding to HA. Accordingly, the amount of HABP binding to HA or a value that reflects the amount can be measured to determine the molecular weight of HA.

The method of the present invention can be performed by the following steps (1) to (3):
(1) measuring a concentration of HA in a sample;
(2) reacting the HA in the sample with a HABP to measure an amount of the HABP that is bound to the HA in the sample or a value that reflects the amount; and
(3) determining a molecular weight of the HA in the sample from: a relationship between the molecular weight of the HA and the amount of the HABP binding to the HA or the value that reflects the amount, the relationship being obtained from a standard HA sample with known concentration and molecular weight; the concentration of the hyaluronic acid in the sample obtained in the step (1); and the amount of the HABP that is bound to the HA in the sample or the value that reflects the amount obtained in the step (2).

As the step (2), there is given a step formed of the following steps (i) to (iv), for example:
(i) immobilizing a HABP to a solid phase;
(ii) reacting the HABP that is immobilized to the solid phase with the HA in a sample;
(iii) further reacting the HA that is bound to the HABP that is immobilized to the solid phase with a labeled HABP; and
(iv) measuring an amount of the labeled HABP that is bound to the HA in the step (iii) or a value that reflects the amount.

As a label substance of the labeled HABP to be used in the step (iii), biotin, avidin, an enzymes, an isotope, a fluorescent pigment, a chemiluminescent substance or the like may be used. Biotin and avidin are preferable.

The relationship between the molecular weight of the HA and the amount of the HABP binding to the HA or the value that reflects the amount, the relationship being used in the step (3) and obtained from the standard HA sample with known concentration and molecular weight, is obtained as a standard curve that is obtained by performing the step (2) using the HA standard solution with known concentration and molecular weight as the sample.

In the step (3), the concentration of the HA in the sample that is obtained in the step (1) is used as an index for dilution of the sample or used for calculation for the amount of the HABP binding to the HA in the standard HA sample at the concentration or the value that reflects the amount.

The reactivity of the labeled HABP with HA as described above, that is, the amount of the labeled HABP binding to HA can be adjusted while maintaining such a characteristic that the reactivity varies depending on the molecular weight of HA by the following: when HABP is bound to HA, additives such as protein denaturants, acidic polysaccharides, and surfactants are allowed to exist and those amounts are regulated. Further, an amount of HABP that is bound to HA to be measured in the step (iv) or a value that reflects the amount can be also adjusted while maintaining such a characteristic that the reactivity varies depending on the molecular weight of HA by changing an amount of HABP to be immobilized in the step (i) or an amount of HABP to be reacted in the step (iii).

Accordingly, for example, when the labeled HABP and a coloring substance associated with the labeled HABP are used in the step (iv) to measure an amount of HABP from the absorbance, appropriate kind and amount of additives as described above are used and/or an amount of HABP to be used in each step is adjusted. Thus, the absorbance to be measured can be adjusted so as to be in a range suitable for the measurement.

As the above additives, there can be used guanidine hydrochloride, protein denaturants such as urea, acidic polysaccharides such as CS—C, surfactants such as SDS, and the like.

Specifically, the amount of HABP to be immobilized is, as the concentration of the HABP solution to be used for the immobilization, 3 ng/mL or more and preferably 10 ng/mL or more and generally 30,000 ng/mL or less, preferably 10,000 ng/mL or less, and more preferably 1,000 ng/mL or less, for example. The amount of the labeled HABP to be reacted in the step (iii) is, in the case of using biotin as a label substance, as the concentration of a biotin-HABP solution to be used for the reaction, 10 ng/mL or more, preferably 100 ng/mL or more, and more preferably 200 ng/mL or more and generally 30,000 ng/mL or less and preferably 3,200 ng/mL or less, for example. In the case where guanidine hydrochloride is used as an additive, the concentration of guanidine hydrochloride in the HA standard solution and/or a sample is, as a final concentration, 0 to 3.6 M and preferably 0 to 2.4 M, for example. The concentration of guanidine hydrochloride in the biotin-HABP solution is, as a final concentration, for example, 0 to 1.6 M and preferably about 0 to 1.2 M, for example.

In another embodiment of the present invention, there is also provided a kit for measurement of a molecular weight of HA including HABP. The kit of the present invention can be used to carry out the method of the present invention described above.

The kit of the present invention may include, in addition to HABP, the above additives, buffers containing the additives, HA standard samples having a known molecular weight, and the like.

EFFECTS OF THE INVENTION

According to the present invention, there is provided a method of measuring a molecular weight of HA in which the molecular weight of HA in a small amount of sample can be measured for a number of samples in a short time. For example, the method is extremely useful in diagnosis in medical care, pharmaceutical development, and other biochemical researches. According to the method, compared with a conventional method for the measurement of the molecular weight of HA, the molecular weight of HA in a smaller amount of sample can be measured for a number of samples in a short time. Therefore, the method is particularly useful in diagnosis in medical care and pharmaceutical development.

BEST MODE FOR CARRYING OUT THE INVENTION

Figure 1:
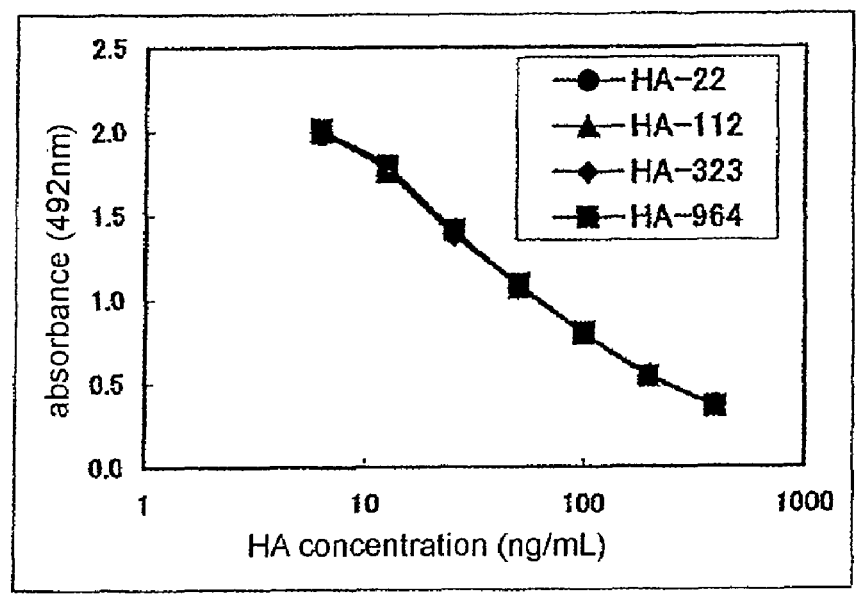
FIG. 1 is graph showing reaction curves of HA's having various molecular weights in measuring the concentrations of HA samples.

A method of measuring a molecular weight of HA of the present invention is characterized by including reacting HA in a sample with HABP to measure an amount of the HABP that is bound to the HA in the sample or a value that reflects the amount.

In the above step, the reactivity of HABP with HA varies in a given direction depending on the molecular weight of HA. Therefore, the molecular weight of HA causes change in an amount of HABP binding to HA. Thus, the amount of HABP binding to HA or the value that reflects the amount can be measured to determine the molecular weight of HA.

According to the method of the present invention, even if a sample contains any contaminants such as proteins, nucleic acids, lipids, and other inorganic compounds, the molecular weight of HA can be measured without influences of such contaminants. Accordingly, the sample containing HA is not necessarily purified, and the sample containing substances other than HA, such as a biological sample, may be also used in the method of present invention.

Specific examples of test specimens to be measured in the method of the present invention include HA solution, cell culture media, organ culture media, body fluids, and tissues. Examples of body fluids include blood, serum, plasma, urine, saliva, synovial fluid, pleural fluid, ascites fluid, bone marrow fluid, spinal fluid, and vitreous fluid. Examples of tissues include cartilage, synovial membrane, skin, and colon. Of those, cell culture media, organ culture media, synovial fluid, cartilage, synovial membrane, skin, and the like are particularly preferable as the test specimens.

In the case where the method of the present invention is applied to the measurement of the molecular weight of HA present in various biological components such as: serum; urea; synovial fluid; tissues such as cartilage, synovial membrane, and skin; and culture media of cultivated cells, a pretreatment can be applied to the test specimens appropriately. As the method for pretreatment, the following methods can be used alone or in combination. Examples thereof include: extraction with salts such as urea, guanidine hydrochloride, and sodium chloride; protein degradation treatment with proteolytic enzymes such as pronase and actinase; removal and neutralization of protein with protein denaturants such as TCA; desalting with a desalting column or dialysis; ion-exchange separation with an ion-exchange column; precipitation with ethanol; and precipitation with quaternary ammonium salts such as cetylpyridinium chloride (CPC) and cetyltrimethylammonium bromide (CETAB). For those pretreatment, it must be confirmed with pilot study that the molecular weight of HA does not reduce due to the pretreatment to be applied and the solvent composition after the pretreatment does not affect the reaction in the steps (1) and (2). The method for pretreatment is not limited to the method as described above as long as the method satisfies those conditions.

Of various methods for the pretreatment as describe above, a method with protease treatment is preferable in view of simpleness. More particularly, the method can be performed by conducting the pretreatment proposed in the following steps 1), 2), and 4) or 1), 2), 3), and 4) sequentially:

1) degrading coexisting protein with protease treatment under the condition that the molecular weight of HA does not decrease;
2) deactivating protease by adding a protein precipitant, denaturant, or specific inhibitor to the treatment solution in the step 1) under the condition that the molecular weight of the HA does not decrease;
3) neutralizing or removing each of the reagents in the step 2) under the condition that the molecular weight of the HA does not decrease;
4) addition of certain ingredient to the solution in the step 2) or 3) to adjust the conditions of the solution for carrying out the molecular weight measurement steps 1 and 2 correctly.

As the combination of each of the steps in the method with protease treatment as described above, there can be used, for example, various combinations as described in Table 35.

The composition of the solvent (substance other than HA) finally obtained by the combination of the pretreatment step as described above varies from the performed treatment condition, and is not particularly limited as long as it is confirmed in advance that the composition satisfies two conditions as described below:

1. exhibiting the same reactivity without being affected by the molecular weight of HA in the step 1 for measurement of the molecular weight; and
2. exhibiting change in the reactivity in a given direction in accordance with increase of the molecular weight of HA in the step 2 for measurement of the molecular weight.

In the above pretreatment step 1), for example, various proteases as described below can be used:
(1) Protease from Bacterial Cell
(for example, Pronase E, Proteinase K (Sigma-Aldrich, Inc.), Actinase E and Actinase AF (Kaken Pharmaceutical Co., Ltd.), and Dispase (Roche Diagnostics K. K.));
(2) Collagenase from Bacterial Cell
(for example, Collagenase A and Collagenase P (Roche Diagnostics K. K.));
(3) Cystein Proteinase from Vertebrate
(for example, Papain); and
(4) Serine Proteinase from Vertebrate
(for example, Chimotrypsin and Trypsin).

In the above pretreatment step 2), various reagents as described below can be used as precipitants/denaturants:
a) reagents for removing a protein such as TCA and perchloric acid;
b) acidic buffers having a pH of 2.0 or less; and
c) protein denaturants such as guanidine hydrochloride, urea, and ammonium sulfate.

In this step, the operation for removing denatured and precipitated proteases may be added as appropriate. Specifically, the operation as described below can be utilized:
a) centrifugation; and
b) filter filtration.

Similarly, in the above pretreatment step 2), for example, various reagents as described below can be used as specific inhibitors:
a) chelating agents (for example, EDTA and EGTA);
b) reductants (for example, iodoacetic acid);
c) Serine Protease inhibitors (for example, TPCK, TLCK, and soybean trypsin inhibitor); and
d) commercially-available protease inhibitor cocktails.

In the case of carrying out the neutralization treatment in the above pretreatment step 3), the method as described below can be utilized:
1) a basic solution prepared with Good's buffer constituents such as Tris, Bis-Tris, and MOPS; and
2) a basic solution prepared with inorganic salts such as sodium borate and sodium phosphate.

In the case of carrying out the removal treatment in the above pretreatment step 3), the methods as described below can be utilized:
1) desalting using a desalting column; and
2) dialysis using a dialysis membrane, dialysis cassette, and the like.

The following methods can be also used to concentrate a sample as appropriate:
1) centrifugal evaporator; and
2) lyophilization.

The molecular weight of HA to which the method of the present invention can be applied is not particularly limited as long as the characteristics that the reactivity of HABP with HA varies in a given direction depending on the molecular weight of HA is maintained. For example, the method can be applied to HA having a molecular weight of 3 kDa or more, preferably 10 kDa or more, and more preferably 20 kDa or more and for example 3,000 kDa or less, and preferably 1,000 kDa or less.

Accordingly, for example, naturally-occurring HA from a variety of sources, and HA of which molecular weight is decreased with alkali treatment, enzyme treatment, and the like may be subjects to be measured in the method of the present invention. Further, salts of HA may be also subjects to be measured in the method of the present invention.

The "HABP" to be used in the method of the present invention is a protein having a property binding to HA. Specific examples thereof include HA-binding proteoglycans (for example, cartilage proteoglycans, digests of cartilage proteoglycans with trypsin, digests of cartilage proteoglycans with chondroitinases A, B, and C (JP 2732718 B)), core proteins of proteoglycans (for example, core proteins of cartilage proteoglycans), link proteins, hyaluronectin, CD44, portion proteins containing HA binding sites of those proteins, or fusion proteins of the portion proteins and other proteins, and antibodies recognizing HA (JP09-12600A). Those may be isolated and purified from natural products, or prepared with gene recombinant technology. Of those, digests of cartilage proteoglycans with trypsin are particularly preferable, and a digest of proteoglycans of bovine nasal cartilage with trypsin are still more preferable. Further, each ingredient in the digests with trypsin can be used after separation and purification. It should be noted that the digests of proteoglycans of bovine nasal cartilage with trypsin is sold by SEIKAGAKU CORPORATION as "HA-binding protein" (digests of proteoglycans of bovine nasal cartilage with trypsin, and a mixture containing (1) an HA binding region (HABR) of Aggrecan, (2) an HA binding region (HABR) of Aggrecan in which a KS-chain-containing domain remains, and (3) link proteins), and those can be preferably used.

The method of the present invention as described above can be preferably carried out by the following steps:
(1) measuring the concentration of HA in a sample;
(2) reacting HA in the sample with HABP to measure an amount of HABP bound to HA in the sample or a value that reflects the amount; and
(3) determining the molecular weight of HA in the sample using the relationship between the molecular weight of HA and an amount of HABP binding to HA or a value that reflects the amount, the relationship being obtained from a standard HA sample with known concentration and molecular weight, the concentration of HA in the sample obtained in the above step (1), and the amount of HABP bound to HA or the value that reflects the amount in the sample obtained in the above step (2).

The above step (1) is a step involved in measuring the concentration of HA in the sample by a quantitative measurement independent of the molecular weight of HA. Examples of the method of carrying out this step include, but not particularly limited to as long as the method is capable of measuring the concentration of HA in the sample: general colorimetric methods such as a carbazole sulfuric acid method; a quantitative method in which an enzyme specifically degrading HA is combined with HPLC or capillary electrophoresis; and a competitive inhibition method utilizing a solid phase on which HA is immobilized and HABP. Of those, the competitive inhibition method utilizing the solid phase on which HA is immobilized and HABP is most preferable because a number of specimens can be measured simultaneously and measurement sensitivity is good.

The competitive inhibition method utilizing the solid phase in which HA is immobilized and HABP can be performed with known methods, for example, the methods described in JP 63-150669 A and JP 2000-97940 A. As the HABP, solid phase, label, and the like to be used, there can be used similar substances as those used in the step (2) described below.

The competitive inhibition method utilizing the solid phase in which HA is immobilized and HABP can be performed according to the specific procedure as described below, for example, but is not limited thereto.
1) HA covalently bound to BSA is immobilized to each well on an ELISA plate.
2) Each well is blocked with BSA.
3) An HA standard sample (having only 1 kind of specified molecular weight and around 6 concentration points) and a test sample diluted appropriately are added to each well.
4) A Biotin-HABP solution is added to the test sample to react for a predetermined time.
5) After removal of unreacted HA and biotin-HABP, a HRP-avidin solution is added to react for a predetermined time.
6) A solution of a coloring substrate (for example, o-phenylenediamine) is added to react for a predetermined time.
7) A stop solution is added and an absorbance is measured at a given measurement wavelength using a microplate absorptiometer.
8) A standard curve is prepared on the basis of the absorbance obtained for the standard sample. The concentration of HA in the test sample is determined from the standard curve and the absorbance obtained for the test sample.

The above step (2) is a step of measuring the reactivity of HABP with HA that varies depending on the molecular weight of HA as an amount of HABP binding to HA or a value that reflects the amount.

In this step, a method of measuring an amount of HABP binding to HA is not particularly limited as long as the purpose of the step as described above is achieved. The method is performed preferably with a sandwich method using the solid phase on which HABP is immobilized and an HABP labeled with any label substance be performed. For example, the measurement can be performed with the following steps:
(i) immobilizing HABP to a solid phase;
(ii) reacting HABP that is immobilized to the solid phase with HA in a sample;
(iii) further reacting the HA that is bound to HABP with a labeled HABP; and
(iv) measuring an amount of the labeled HABP that is bound to the HA in the step (iii) or a value that reflects the amount.

The measurement of HABP using the sandwich method as described above can be performed according to a known method. AS examples of the known method, there can be seen the measurement of HABP in the method of measuring HA described in JP 06-41952 B.

The solid phase to be used in the above step (i) is not particularly limited with respect to the shape, material, and the like as long as the solid phase is a water-insoluble solid phase capable of immobilizing HABP. Examples thereof include plates (for example, wells of microplates) made of material such as polystyrene, polypropylene, nylon, and polyacrylic amide, tubes, beads, membranes, gels, and latexes. Of those, the wells of microplates made of polystyrene can be preferably used.

As the method of immobilizing HABP to those solid phases, a common method as a method for preparation of immobilized enzymes can be applied, such as a physical adsorption method, a covalent attachment method, and an entrapment method (see Immobilized enzyme, 1975, published by Kodansha Ltd., pp. 9 to 75). Of those, the physical adsorption method is preferable because the method has a simple operation and has been used frequently.

An specific example of the physical adsorption method include a method in which HABP is dissolved in a buffer having a pH of about 6 to 9 (for example, phosphate buffer, PBS, and carbonate buffer), added to a solid phase, and left to stand at 4° C. overnight to carry out the immobilization. The method can be preferably used.

It should be noted that, after that, a blocking substance is preferably added to the solid phase to coat a portion in which HABP is not immobilized. Examples of the blocking substance include serum albumin such as BSA, casein, skim milk, and gelatin. Further, there can be also used a commercially-available blocking substance.

The method as described above can be used to produce the solid phase in which HABP is immobilized. The production of the solid phase may be performed per test, or reservable dry plates may be prepared and used.

The above step (ii) is performed by contacting the HABP-immobilized solid phase produced as described above with a test specimen to be measured described above. Specifically, the step can be performed as follows. That is, the test specimen is added to the HABP-immobilized solid phase and incubated at 0 to 45° C. and preferably at about 37° C. for 30 minutes to 1 hour, for example.

Following the reaction, it is preferable that the surface of the solid phase be washed with a washing solution. The washing is performed under the condition that HABP immobilized to the solid phase and HA bound to the HABP would not be detached. As the washing solution, there can be preferably used, for example, buffers added with nonionic surfactants such as Tween surfactants (for example, PBS and Tris-HCl buffer).

The above step (iii) can be performed with the method and reaction condition similar to those in the step (ii).

As the label substance for the labeled HABP to be used in the above step (iii), there can be used, for example, biotin, avidin, enzymes, isotopes, fluorescent pigments, and chemiluminescent substances. Of those, biotin and avidin are preferable because they have good handleability and an amount of the substance to be labeled is correctly reflected, for example. Further, an antibody for HABP is prepared, labeled with the label substance as described above, and reacted with HABP, whereby HABP can be detected.

Also for the solid phase after the reaction in the above step (iii), the surface of the solid phase is preferably washed with the washing solution in the same manner as in the above step (ii).

The above step (iv) can be performed with a known method in accordance with the used label. For example, in the case of using biotin as the label substance, there can be given the following method. That is, an enzyme (for example, peroxidase) bound to avidin is added to bind biotin to avidin. Then, a substrate, a coloring substrate, and the like for enzymes, which is bound to streptavidin etc., are added. After that, the degree of coloring of the product derived from an enzyme reaction is measured on the basis of the change in the absorbance. Further, in the case of using a fluorescent substance and a chemiluminescent substance, there is given, for example, a method of measuring the fluorescence and the luminescence after the reaction.

More specifically, the step (iv) can be performed in the case of using biotin as the label substance as follows. That is, an HRP-avidin solution is added to the solid phase after the reaction in the above step (iii) and reacted at 37° C. for 1 hour, for example, followed by washing. The solid phase is then added with an o-phenylenediamine solution, and reacted under the protection from light at room temperature for 30 minutes, for example. After that, the absorbance of the reaction solution can be measured at an absorption wavelength of 492 nm and a reference wavelength of 630 nm.

In addition, the reactivity of HABP with HA as described above, that is, an amount of HABP that is bound in the above step (iii) or a value that reflects the amount can be adjusted, while maintaining the characteristic that the reactivity varies depending on the molecular weight of HA, by adding additives such as protein denaturants, acidic polysaccharides, and surfactants and regulating the amounts of the additives at the reaction in the step (iii).

As the additives as described above, there can be used guanidine hydrochloride, protein denaturants such as urea, acidic polysaccharides such as CS-C, and surfactants such as SDS, for example. Of those, guanidine hydrochloride is particularly preferable.

For an amount of the additives, in the case of using guanidine hydrochloride, in view of obtaining good reactivity depending on the molecular weight and concentration of HA, the concentration of guanidine hydrochloride in the HA standard solution and/or the sample as described above is 0 to 3.6 M and preferably 0 to 2.4 M, for example, at a final concentration. The concentration of guanidine hydrochloride in a biotin-HABP solution is 0 to 1.6 M and preferably about 0 to 1.2 M, for example, at a final concentration (see Examples as described below). However, the concentration is not limited thereto.

Further, an amount of HABP that is bound to HA to be measured in the step (iv) or a value that reflects the amount can be also adjusted, while maintaining the characteristic that the reactivity varies depending on the molecular weight of the HA, by changing an amount of HABP to be immobilized in the step (i) or an amount of HABP to be reacted in the step (iii). Accordingly, it is preferable that the reactivity and reaction amount suitable for the measurement be obtained by appropriately setting those conditions. Further, there is preferably used a method in which the reactivity is controlled so that HA having higher molecular weight has higher reactivity within the molecular weight range of interest.

Examples of a specific amount of HABP to be immobilized in the step (i) include, but are not limited to, 3 ng/mL or more and preferably 10 ng/mL or more and generally 30,000 ng/mL or less, preferably 10,000 ng/mL or less, and more preferably 1,000 ng/mL or less as the concentration of an HABP solution used for the immobilization in view of obtaining good reactivity depending on the molecular weight and concentration of HA (see examples as described below).

Examples of a specific amount of the labeled HABP to be reacted in the step (iii), in the case of using biotin as a label substance include, but are not limited to, 10 ng/mL or more, preferably 100 ng/mL or more, and more preferably 200 ng/mL or more and generally 30,000 ng/mL or less and preferably 3,200 ng/mL or less as the concentration of an biotin-HABP solution used in the reaction in view of obtaining good reactivity depending on the molecular weight and concentration of HA (see examples as described below).

The above step (3) is a step of determining the molecular weight of HA from the relationship between the molecular weight of HA obtained from standard HA samples with known concentration and molecular weight and an amount of HABP binding to HA or a value that reflects the amount, the concentration of HA in the sample obtained in the above step (1), and the amount of HABP that is bound to HA in the sample obtained in the above step (2).

The relationship between the molecular weight of HA obtained from standard HA samples with known concentration and molecular weight and an amount of HABP binding to HA or a value that reflects the amount, which is used in the above step (3), can be obtained as a standard curve by performing the step (2) using HA standard solution with known concentration and molecular weight as a sample.

In other words, a plurality of standard HA samples with known concentration and molecular weight are used to perform the step (2). As a value that reflects the amount of the labeled HABP that is bound to HA in the reaction with each sample, for example, there is measured the absorbance of the reaction solution obtained through the coloring reaction to be performed using the label. Those absorbances are plotted against the molecular weight of each of the standard HA samples to afford a standard curve. Then, the molecular weight of HA in the test sample is determined by applying the value obtained with the measurement in the step (2) for the test sample to the obtained standard curve.

As the concentration in the case where the standard HA sample is measured, the concentration of the test sample measured in the step (1) is used as an index. The concentration of the test sample itself or the concentration obtained by appropriately diluting the test sample is used. The measurement in the step (2) and the measurement for the preparation of the standard curve are performed at the same concentration of HA. As a result, the concentration can be determined by applying the value obtained with the measurement in the step (2), as it is, to the standard curve. In that case, there need to perform the steps (1) and (2) step-by-step and to determine the concentration of HA in the test sample beforehand (see Example 16 as described below).

Alternatively, even when the steps (1) and (2) are performed simultaneously with respect to both the standard sample and the test sample, if the concentration of HA in the test sample and an amount of HABP that is bound to HA or a value that reflects the amount can be measured under the measurement condition set for the standard sample in each step, the standard curve at any concentration can be determined by the conversion on the basis of the reaction curves for the standard samples having different molecular weights determined in the step (2). The standard curve can be used to determine the molecular weight of HA in the test sample (see Example 17 as described below).

In addition, in the case where the reproducibilities of the standard curve for the measurement of the concentration of HA in the sample in the step (1), and the standard curve representing the relationship between the molecular weight of HA and the amount of HABP binding to HA or the value that reflects the amount are ensured sufficiently, the preparation for those standard curves in advance makes the following possible. That is, only the test sample is subjected to the steps (1) and (2), and the resulting value is used to perform the step (3). As a result, the molecular weight of HA can be determined, and the molecular weight of HA in a small amount of test sample can be easily determined for a number of samples in a short time.

In the standard curve, on the basis of the value obtained for the standard HA sample, the molecular weight can be expressed as a linear, quadratic or higher-dimensional function of the value that reflects the amount of the labeled HABP that is bound to HA, such as the absorbance or the logarithmic value thereof, and the concentration of HA or the logarithmic value thereof as the case may be. The molecular weight of HA can be determined by applying a value such as the absorbance obtained for the sample or the logarithmic value thereof to the function. In any case, for the standard curve, the preparation for a plurality of the standard curves corresponding to the concentration and molecular weight of HA to be expected in the test sample allows more rapid and correct measurement.

From the foregoing, the steps (2) and (3) including the relationship between the molecular weight of HA to be used in the step (3) and an amount of HABP binding to HA and a value that reflects the amount can be performed according to the procedure as described below, for example.

9) HABP is immobilized to each well of an ELISA plate.
10) Each well is blocked with BSA.
11) The standard sample (having 3 or more kinds of specified molecular weights and the same 1 concentration point) and the test sample are added to each well to react for a predetermined time.
12) A solution of biotin-HABP is added and reacted for a predetermined time.
13) A solution of HRP-avidin is added and reacted for a predetermined time.
14) A solution of a coloring substrate (for example, o-phenylenediamine) is added to react for a predetermined time.
15) A stop solution is added and the absorbance is measured at a given measurement wavelength using a microplate absorptiometer.
16) The absorbance obtained for the standard sample is used to plot the absorbance against the molecular weight to prepare a standard curve. The standard curve and absorbance obtained for the test sample determines the molecular weight in the test sample.

The present invention further provides a kit for the measurement of the molecular weight of HA including HABP to be used in the method of measuring the molecular weight of HA of the present invention.

The kit of the present invention described above, in addition to HABP, may include an additive for the regulation of the reactivity of HABP with HA, a buffer with or without the additive, and an HA standard sample having known molecular weight for the preparation of the standard curve.

It should be noted that, in this description, unless stated otherwise, the terms "molecular weight" and "average molecular weight" mean "weight average molecular weight".

EXAMPLE

The present invention is herein after described by way of Examples, however the present invention is not limited to Examples described below.

Materials

The following materials were used in the following examples.

96-well plate for ELISA (Maxisorp, manufactured by NALGENUNC)
BSA (manufactured by Oriental Yeast Co., Ltd.)
HA (Alts ampoule, derived from Cock's comb, manufactured by SEIKAGAKU KOGYO CO., LTD.)
CS—C (derived from shark cartilage, manufactured by SEIKAGAKU KOGYO CO., LTD.)
HA-BSA (manufactured by SEIKAGAKU KOGYO CO., LTD.)
HABP ("hyaluronic acid-binding protein", manufactured by SEIKAGAKU KOGYO CO., LTD.)
Biotin-HABP (manufactured by SEIKAGAKU KOGYO CO., LTD.)
HRP-avidin (manufactured by PIERCE Corp.)
OPD tablet (manufactured by Sigma-Aldrich Corp.)
ABTS tablet (manufactured by Sigma-Aldrich Corp.)
Buffer for OPD (o-phenylenediamine) (manufactured by Institute of Immunology Co., Ltd.)
TMB (+) (manufactured by DAKO)
TMB BLUE (manufactured by DAKO)
PBS (prepared by dissolving 8 g of sodium chloride, 0.2 g of potassium chloride, 2.9 g of disodium dihydrogen phosphate, and 0.2 g of potassium dihydrogen phosphate in 1 liter of purified water)

Washing solution (prepared by adding 0.5 mL of Tween-20 (manufactured by Wako Pure Chemical Industries, Ltd.) to 1 L of PBS and dissolving the mixture under stirring)

ELISA basic buffer (10 g of BSA were added to 1 L of washing solution, the mixture was dissolved under stirring, and the resultant was filtered with a filter having a pore size of 0.2 μm to prepare the buffer.)

Preparation for HA's Having Various Molecular Weights

The above HA derived from cock's comb (referred to as sample A) was treated under the alkali condition (having a pH of 10.5) or with sheep testicular hyaluronidase to make the molecule weight low and purified with ethanol precipitation treatment to prepare the following samples B to J. Each of the described molecular weights was a value measured by a GPC method in Example 1 as described below. Those samples were used as test samples for the test in Example 2 or later.

Sample A: 2,289 kDa (herein after, also referred to as "HA-2289")
Sample B: 964 kDa (herein after, also referred to as "HA-964")
Sample C: 821 kDa (herein after, also referred to as "HA-821")
Sample D: 606 kDa (herein after, also referred to as "HA-606")
Sample E: 323 kDa (herein after, also referred to as "HA-323")
Sample F: 248 kDa (herein after, also referred to as "HA-248")
Sample G: 182 kDa (herein after, also referred to as "HA-182")
Sample H: 112 kDa (herein after, also referred to as "HA-112")
Sample I: 61 kDa (herein after, also referred to as "HA-61")
Sample J: 22 kDa (herein after, also referred to as "HA-22")

Example 1

Measurement of Molecular Weight of HA by GPC Method

The HA derived from cock's comb was used to prepare HA standards for GPC. The molecular weight of the HA was made low by the above method. The resultant was purified with ethanol precipitation to afford 9 kinds of standards (HA-MWSTD-1 to HA-MWSTD-9). Those molecular weights were determined by a light scattering method, which was a known method.

The concentration of each of 9 kinds of the standards for GPC and 10 kinds of the test samples as described above was adjusted to about 100 μg/mL using 0.2 M NaCl, followed by the analysis under the following conditions. The molecular weight of the standards and the dissolution time at the dissolution peak position were plotted on X- and Y-axis, respectively, to prepare the standard curve. The standard curve was used to calculate the peak molecular weight of the test samples from the dissolution peak position for the test samples.

Measuring Device
Column oven: CO-8025 (manufactured by TOSOH CORPORATION)
Pump: PU-920 (manufactured by Jasco Corporation)
Ultra violet absorption detector: UV-1575 (manufactured by Jasco Corporation)
Column: TSK-GEL G-6000PWXL (manufactured by TOSOH CORPORATION)
Measurement Conditions
Solvent: 0.2 M NaCl Temperature: 40° C.

Flow rate: 0.5 mL/min.

Detection condition: Ultra violet absorption at a wavelength of 215 nm

The test was performed twice (Tests 1 and 2). The measurement was performed with Tests 1 and 2 for 9 kinds of the standards for GPC and the samples B, H, and J, Test 1 for the samples A, E to G, and I, and Test 2 for the samples C and D. In each test, the measurement was performed with n=3 all for the molecular weight standards for GPC and n=2 all for each test sample. The results are shown in Table 1.

TABLE 1

Test 1

| Standard | Retention time (minutes) | CV | Molecular weight (kDa) |
|---|---|---|---|
| HA-MWSTD-1 | 14.8 | 0.7% | 2,310 |
| HA-MWSTD-2 | 15.3 | 0.1% | 1,410 |
| HA-MWSTD-3 | 16.3 | 0.3% | 993 |
| HA-MWSTD-4 | 16.5 | 0.2% | 847 |
| HA-MWSTD-5 | 17.5 | 0.3% | 637 |
| HA-MWSTD-6 | 18.2 | 0.2% | 460 |
| HA-MWSTD-7 | 20.9 | 0.1% | 104 |
| HA-MWSTD-8 | 21.8 | 0.0% | 64 |
| HA-MWSTD-9 | 23.2 | 0.1% | 18.9 |

| Test sample | Retention time (minutes) | CV | Molecular weight measurements (kDa) |
|---|---|---|---|
| A | 14.6 | 0.7% | 2,289 |
| B | 16.4 | 0.0% | 964 |
| E | 18.9 | 0.3% | 323 |
| F | 19.5 | 0.1% | 248 |
| G | 20.1 | 0.0% | 182 |
| H | 20.9 | 0.1% | 112 |
| I | 21.8 | 0.3% | 61 |
| J | 23.1 | 0.1% | 22 |

Test 2

| Standard | Retention time (minutes) | CV | Molecular weight (kDa) |
|---|---|---|---|
| HA-MWSTD-1 | 14.9 | 0.3% | 2,310 |
| HA-MWSTD-2 | 15.3 | 0.2% | 1,410 |
| HA-MWSTD-3 | 16.2 | 0.3% | 993 |
| HA-MWSTD-4 | 16.5 | 0.1% | 847 |
| HA-MWSTD-5 | 17.4 | 0.1% | 637 |
| HA-MWSTD-6 | 18.3 | 0.3% | 460 |
| HA-MWSTD-7 | 20.9 | 0.1% | 104 |
| HA-MWSTD-8 | 21.8 | 0.2% | 64 |
| HA-MWSTD-9 | 23.2 | 0.1% | 18.9 |

| Test sample | Retention time (minutes) | CV | Molecular weight measurements (kDa) |
|---|---|---|---|
| C | 16.7 | 0.2% | 821 |
| D | 17.4 | 0.2% | 606 |
| B (Confirmation for reproducibility) | 16.4 | 0.2% | 956 |
| H (Confirmation for reproducibility) | 20.9 | 0.1% | 115 |
| J (Confirmation for reproducibility) | 23.0 | 0.0% | 23 |

The molecular weight shown for the standard in Table 1 is the molecular weight measured by the light scattering method.

The time required for the measurement in the present Example was 47 hours for Test 1 and 37 hours for Test 2. As described above, the GPC method, which is one of the existing methods, requires a long time because only 1 sample can be analyzed per 1 cycle. Further, there are required the amount of HA of 40 μg or more (400 μL of a 100 μg/mL solution).

Example 2

Quantitative Measurement of HA Concentration by HPLC Method

For samples A to J each of which was measured for the molecular weight by the GPC method in Example 1, the concentration of HA was quantitatively measured by the HPLC method as described below.

Standard

An HA unsaturated disaccharide standard (manufactured by SEIKAGAKU CORPORATION) was dissolved in purified water, and the resultant was measured with a spectrophotometer (U-530DS; manufactured by JASCO Corporation) in which the ultra violet absorption at a wavelength of 232 nm was calibrated. The concentration was determined on the basis of the substance having the molecular extinction coefficient of 5.7. The substance was diluted correctly using a calibrated electronic scale (AT-250; manufactured by Mettler Toledo International Inc.) to prepare the standard solution for HPLC quantitative measurement having a concentration of 2 μg/mL.

Measuring Device

Pump: PU-2080 (manufactured by Jasco Corporation)

Gradient Unit: (manufactured by Jasco Corporation)

Autosampler: AS-2050 (manufactured by Jasco Corporation)

Heating reactor: DB-5 (manufactured by Shimamura Instruments, Works, Co.)

Phosphor detector: FP-2059 (manufactured by Jasco Corporation)

Column: YMC-GEL PA120-S05 (manufactured by YMC Co., LTd.)

Measurement Conditions

Solvent: 0 to 200 mM $Na_2SO_4$ gradient

Temperature: Room temperature

Flow rate: 0.5 mL/min.

Labeled temperature: 145° C.

Detection conditions: Excitation wavelength of 346 nm, absorption wavelength of 410 nm Method of Measuring HA Concentration The test sample was collected, added with Hyaluronidase SD (manufactured by SEIKAGAKU CORPORATION) so as to achieve a final concentration of 100 mU, and added with a sodium acetate buffer so as to achieve a final concentration of 25 mU. The resultant was reacted at 37° C. for 2 hours and completely degraded to HA unsaturated disaccharide. The resulting digestion solution of the test sample and the HA unsaturated disaccharide standard solution were analyzed by HPLC under the above conditions. On the basis of the ratio of the peak area of the standard solution to the area of the test sample digestion solution, the concentration of HA's having various molecular weights, which were the test samples, was calculated. The results are shown in Table 2.

TABLE 2

| Test sample | Molecular weight measurements (kDa) | HA concentration quantitative values (µg/mL) |
|---|---|---|
| A | 2,289 | 89.5 |
| B | 964 | 111.7 |
| C | 821 | 99.4 |
| D | 606 | 100.9 |
| E | 323 | 143.4 |
| F | 248 | 104.0 |
| G | 182 | 139.7 |
| H | 112 | 93.5 |
| I | 61 | 93.1 |
| J | 22 | 87.7 |

Example 3

Measurement of HA Concentration in Sample (Step (1))

Samples B (HA-964), E (HA-323), H (HA-112), and J (HA-22), each of which was measured for the molecular weight by the GPC method in Example 1 and was measured for the concentration of HA by the HPLC method in Example 2, were adjusted to the concentrations of 0, 6.25, 12.5, 25, 50, 100, 200, and 400 ng/mL. The quantitative test for HA was performed by the competitive ELISA method according to the following procedure.

HA-BSA was dissolved in PBS at a concentration of 100 µg/mL. To each well of a 96-well plate, 100 µL each of the resultant was added and left to stand at 4° C. overnight to carry out the immobilization. After that, each well was washed three times with 300 µL of PBS. Each well was added with 200 µL of a PBS solution containing 1% BSA and left to stand at room temperature for 2 hours to carry out the blocking. Then, each well was washed three times with 300 µL of a washing solution. Each well was added with 50 µL of diluted series of each sample HA prepared with an ELISA basic buffer as described above or a solution without HA. Then, each well was added with 50 µL of biotin-HABP solution prepared with the ELISA basic buffer and reacted at 37° C. for 1 hour, following which each well was washed three times with 300 µL of the washing solution. Each well was added with 100 µL of HRP-avidin solution diluted with the ELISA basic buffer and reacted at 37° C. for 1 hour, following which each well was washed five times with 300 µL of the washing solution. Each of those wells was added with 100 µL of an OPD solution adjusted with a buffer for OPD so as to achieve a concentration of 0.25 mg/mL and reacted under protection from light at room temperature for 30 minutes. Then, each well was added with 100 µL of a 1 M HCl solution. The absorbance was measured at an absorption wavelength of 492 nm and a reference wavelength of 630 nm using an ELISA plate absorptiometer (SK-603, manufactured by SEIKAGAKU CORPORATION). The measurement results and the graphs with the results being plotted are shown in Table 3 and in FIG. 1, respectively.

TABLE 3

| | Sample | | | |
|---|---|---|---|---|
| | J | H | E | B |
| HA | HA Molecular weight (kDa) | | | |
| Concentration (ng/mL) | 22 | 112 | 323 | 964 |
| | Absorbance (492 nm) | | | |
| 0 | 2.254 | 2.254 | 2.274 | 2.281 |
| 6.25 | 1.982 | 1.996 | 1.993 | 2.011 |
| 12.5 | 1.789 | 1.763 | 1.761 | 1.793 |
| 25 | 1.397 | 1.420 | 1.380 | 1.412 |
| 50 | 1.080 | 1.071 | 1.086 | 1.094 |
| 100 | 0.790 | 0.797 | 0.792 | 0.799 |
| 200 | 0.539 | 0.554 | 0.550 | 0.539 |
| 400 | 0.369 | 0.362 | 0.362 | 0.362 |

As apparent from the above results, it was revealed that the competitive ELISA method as described in the present Example could be used to quantitatively measure HA in a simple manner without receiving the influence of the molecular weight with respect to HA having a molecular weight of at least about 20 kDa to 960 kDa.

Example 4

Figure 2:
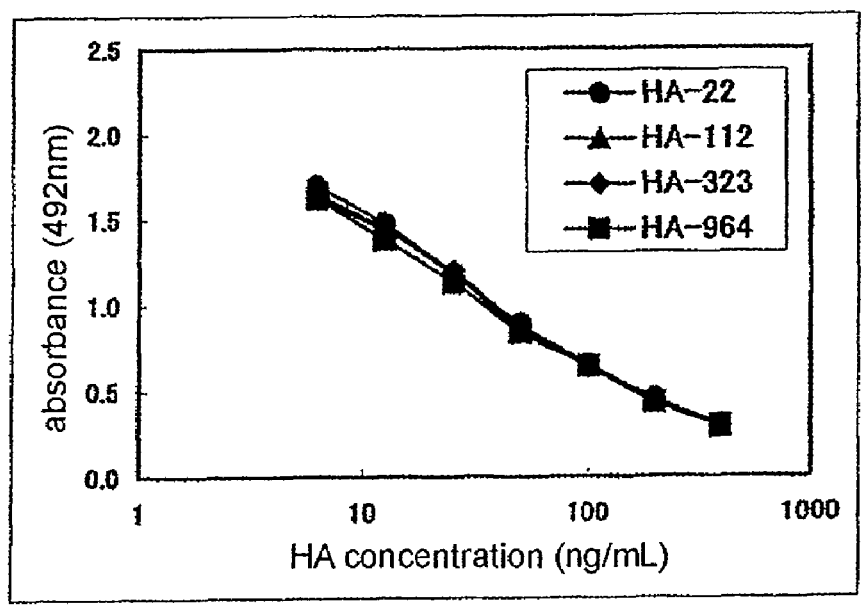
FIG. 2 is graph showing reaction curves of HA's having various molecular weights in the case where a measurement of concentrations of HA samples was performed with change of buffer conditions.
Figure 3:
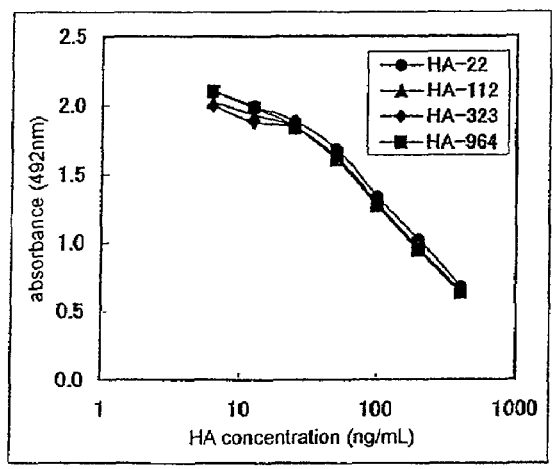
FIG. 3 is graph showing reaction curves of HA's having various molecular weights in the case where the measurement of concentrations of HA samples was performed with change of buffer conditions.

The quantitative test for HA was performed using a method in the same manner as that in Example 3. It should be noted that solutions for the dissolution of biotin-HABP were used as ELISA basic buffers each containing 0.4 M and 1.2 M guanidine hydrochloride. The measurement results and the graphs with the results being plotted are shown in Tables 4 and 5, and in FIGS. 2 and 3, respectively.

TABLE 4

| | Sample | | | |
|---|---|---|---|---|
| | J | H | E | B |
| HA | HA Molecular weight (kDa) | | | |
| Concentration (ng/mL) | 22 | 112 | 323 | 964 |
| | Absorbance (492 nm) | | | |
| 0 | 1.894 | 1.935 | 1.975 | 1.851 |
| 6.25 | 1.696 | 1.649 | 1.621 | 1.625 |
| 12.5 | 1.478 | 1.450 | 1.438 | 1.383 |
| 25 | 1.183 | 1.174 | 1.197 | 1.129 |
| 50 | 0.889 | 0.859 | 0.869 | 0.839 |
| 100 | 0.653 | 0.648 | 0.638 | 0.641 |
| 200 | 0.453 | 0.454 | 0.441 | 0.429 |
| 400 | 0.300 | 0.289 | 0.292 | 0.293 |

TABLE 5

| | Sample | | | |
|---|---|---|---|---|
| | J | H | E | B |
| HA | HA Molecular weight (kDa) | | | |
| Concentration (ng/mL) | 22 | 112 | 323 | 964 |
| | Absorbance (492 nm) | | | |
| 0 | 2.125 | 2.153 | 2.159 | 2.184 |
| 6.25 | 2.104 | 2.024 | 1.996 | 2.100 |
| 12.5 | 1.996 | 1.932 | 1.879 | 1.983 |
| 25 | 1.883 | 1.837 | 1.833 | 1.846 |
| 50 | 1.683 | 1.606 | 1.622 | 1.624 |
| 100 | 1.336 | 1.270 | 1.270 | 1.291 |

TABLE 5-continued

| HA | Sample | | | |
|---|---|---|---|---|
| | J | H | E | B |
| | HA Molecular weight (kDa) | | | |
| Concentration (ng/mL) | 22 | 112 | 323 | 964 |
| | Absorbance (492 nm) | | | |
| 200 | 1.022 | 0.943 | 0.956 | 0.955 |
| 400 | 0.677 | 0.630 | 0.639 | 0.630 |

As apparent from the results of Examples 3 and 4, in the case of applying the competitive ELISA method in the step (1), because the buffer condition etc. does not affect the quantitative measurement of HA's having various molecular weights, the measurement can be performed under a variety of conditions. In other words, the following was confirmed. Even if the optimum condition was appropriately selected for the additives which might change the reactivity in the step (2) as described below in terms of measurement sensitivity, measurement accuracy, stability, operativity, and the like, and the same condition was used to perform the step (1), the measurement results were not affected. Accordingly, for example, the same buffer in the steps (1) and (2) can be used. The conditions on the method of the present invention can be more simplified, and besides, a simpler kit for measurement of the present invention can be constructed.

Example 5

Measurement of Labeled HABP Binding to HA (Step (2))

The labeled HABP binding to HA was measured in accordance with the procedure as described below.

In the present Example, in order to investigate the amount of HABP to be immobilized to a solid phase, a buffer condition at the reaction, and a condition of an additive, the amount of HABP to be immobilized to the solid phase was changed, and for an HA standard solution and a buffer for dissolving biotin-HABP, 5 kinds of ELISA buffers were used as described below.
1) ELISA basic buffer
2) ELISA basic buffer added with 1 M NaCl
3) ELISA basic buffer added with 3 M NaCl
4) ELISA basic buffer added with 0.4 M guanidine hydrochloride
5) ELISA basic buffer added with 1.2 M guanidine hydrochloride HABP was dissolved in PBS in concentrations of 300 and 3,000 ng/mL. Each well of a 96-well plate was added with 100 μL each of the solution and left to stand at 4° C. overnight to carry out the immobilization. After that, each well was washed three times with 300 μL of PBS. Each well was added with 200 μL of PBS solution containing 1% BSA and left to stand at room temperature for 2 hours to carry out the blocking, following which each well was washed three times with 300 μL of a washing solution. Each of those wells was added with 100 μL of 1,000 ng/mL solution of sample J (HA-22) or sample B (HA-964) prepared with each ELISA buffer as described above or a solution without HA, and the resultant was reacted at 37° C. for 1 hour. Then, each well was washed three times with 300 μL of the washing solution. Each of those wells was added with 100 μL of 200 and 800 ng/mL solutions of biotin-HABP prepared with each ELISA buffer as described above, and the resultant was reacted at 37° C. for 1 hour. Then, each well was washed three times with 300 μL of the washing solution. Each of those wells was added with 100 μL of a 500 ng/mL solution of HRP-avidin prepared with ELISA basic buffer, and the resultant was reacted at 37° C. for 1 hour. Each well was washed five times with 300 μL of the washing solution. Each of those wells was added with 100 μL of an OPD solution adjusted with a buffer for OPD so as to achieve a concentration of 0.25 mg/mL and reacted under protection from light at room temperature for 30 minutes. Then, each well was added with 100 μL of a 1M HCl solution. The absorbance was measured at an absorption wavelength of 492 nm and a reference wavelength of 630 nm using an ELISA plate absorptiometer (SK-603, manufactured by SEIKAGAKU CORPORATION). The results are shown in Tables 6 and 7.

TABLE 6

| Reaction condition | 1 | 2 | 3 | 4 | 5 | 6 | 7 | 8 | 9 | 10 | 11 | 12 |
|---|---|---|---|---|---|---|---|---|---|---|---|---|
| HABP immobilization concentration (ng/mL) | 300 | 300 | 300 | 300 | 300 | 300 | 300 | 300 | 300 | 3,000 | 3,000 | 3,000 |
| Kind of additives added to HA standard solution | None | NaCl | NaCl | Guanidine hydrochloride | Guanidine hydrochloride | NaCl | NaCl | Guanidine hydrochloride | Guanidine hydrochloride | None | NaCl | NaCl |
| Concentration of additives added to HA standard solution | | 1 M | 3 M | 0.4 M | 1.2 M | 1 M | 3 M | 0.4 M | 1.2 M | | 1 M | 3 M |
| Biotin-HABP concentration (ng/mL) | 200 | 200 | 200 | 200 | 200 | 800 | 800 | 800 | 800 | 200 | 200 | 200 |

| | 13 | 14 | 15 | 16 | 17 | 18 |
|---|---|---|---|---|---|---|
| HABP immobilization concentration (ng/mL) | 3,000 | 3,000 | 3,000 | 3,000 | 3,000 | 3,000 |
| Kind of additives added to HA standard solution | Guanidine hydrochloride | Guanidine hydrochloride | NaCl | NaCl | Guanidine hydrochloride | Guanidine hydrochloride |
| Concentration of additives added to HA standard solution | 0.4 M | 1.2 M | 1 M | 3 M | 0.4 M | 1.2 M |

TABLE 6-continued

| | | | | | | |
|---|---|---|---|---|---|---|
| Biotin-HABP concentration (ng/mL) | 200 | 200 | 800 | 800 | 800 | 800 |

A biotin-HABP solution was tested without additives.

Reaction proportion of HA's having various molecular weights

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Absorbance of blank | 0.669 | 0.896 | 1.039 | 0.829 | 1.062 | 1.391 | 1.621 | 1.420 | 1.557 | 0.763 | 1.022 | 1.046 | 0.878 | 1.197 | 1.740 | 1.810 | 1.656 | 1.867 |
| HA-22·Absorbance of HA-22 at concentration of 1,000 ng/mL | 1.822 | 1.760 | 1.660 | 1.847 | 1.568 | 2.352 | 2.236 | 2.402 | 2.054 | 1.871 | 1.794 | 1.689 | 1.736 | 1.766 | 2.434 | 2.419 | 2.434 | 2.320 |
| HA-964·Absorbance of HA-964 at concentration of 1,000 ng/mL | 1.940 | 2.068 | 2.034 | 2.170 | 2.077 | 2.395 | 2.399 | 2.431 | 2.472 | 2.138 | 2.037 | 1.978 | 2.058 | 2.058 | 2.397 | 2.422 | 2.413 | 2.407 |
| Absorbance ratio of HA-22 to HA-964 | 91% | 74% | 62% | 76% | 50% | 96% | 79% | 97% | 54% | 81% | 76% | 69% | 73% | 66% | 106% | 100% | 103% | 84% |

* Calculation was made with a value obtained by subtracting the absorbance of the blank.

TABLE 7

Reaction condition

| | 19 | 20 | 21 | 22 | 23 | 24 | 25 | 26 | 27 | 28 | 29 | 30 |
|---|---|---|---|---|---|---|---|---|---|---|---|---|
| HABP immobilization concentration (ng/mL) | 300 | 300 | 300 | 300 | 300 | 300 | 300 | 300 | 300 | 3,000 | 3,000 | 3,000 |
| Biotin-HABP concentration (ng/mL) | 200 | 200 | 200 | 200 | 200 | 800 | 800 | 800 | 800 | 200 | 200 | 200 |
| Kind of additives added to biotin-HABP solution | None | NaCl | NaCl | Guanidine hydrochloride | Guanidine hydrochloride | NaCl | NaCl | Guanidine hydrochloride | Guanidine hydrochloride | None | NaCl | NaCl |
| Concentration of additives added to biotin-HABP solution | | 1 M | 3 M | 0.4 M | 1.2 M | 1 M | 3 M | 0.4 M | 1.2 M | | 1 M | 3 M |

| | 31 | 32 | 33 | 34 | 35 | 36 |
|---|---|---|---|---|---|---|
| HABP immobilization concentration (ng/mL) | 3,000 | 3,000 | 3,000 | 3,000 | 3,000 | 3,000 |
| Biotin-HABP concentration (ng/mL) | 200 | 200 | 800 | 800 | 800 | 800 |
| Kind of additives added to biotin-HABP solution | Guanidine hydrochloride | Guanidine hydrochloride | NaCl | NaCl | Guanidine hydrochloride | Guanidine hydrochloride |
| Concentration of additives added to biotin-HABP solution | 0.4 M | 1.2 M | 1 M | 3 M | 0.4 M | 1.2 M |

An HA standard solution was tested without additives.

Reaction proportion of HA's having various molecular weights

| | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| Absorbance of blank | 0.658 | 0.205 | 0.154 | 0.196 | 0.019 | 0.388 | 0.638 | 0.436 | 0.089 | 0.760 | 0.359 | 0.207 | 0.376 | 0.031 | 0.696 | 0.495 | 0.768 | 0.090 |
| HA-22·Absorbance of HA-22 at concentration of 1,000 ng/mL | 1.727 | 0.879 | 0.259 | 1.021 | 0.035 | 1.652 | 1.140 | 1.615 | 0.230 | 1.930 | 1.286 | 0.399 | 1.377 | 0.114 | 2.110 | 1.036 | 2.297 | 0.443 |
| HA-964·Absorbance of HA-964 at concentration of 1,000 ng/mL | 2.084 | 1.753 | 0.363 | 1.924 | 0.159 | 2.317 | 1.646 | 2.355 | 1.140 | 2.263 | 1.867 | 0.660 | 1.988 | 0.296 | 2.507 | 1.767 | 2.527 | 1.206 |
| Absorbance ratio of HA-22 to HA-964 | 75% | 44% | 50% | 48% | 11% | 66% | 50% | 61% | 13% | 78% | 61% | 42% | 62% | 31% | 78% | 43% | 87% | 32% |

* Calculation was made with a value obtained by subtracting the absorbance of the blank.

The above results revealed the following. In the case of performing the sandwich method in which HA is detected by sandwiching HA between HABP immobilized to the solid phase and biotin-HABP in a liquid phase, the reactivity with biotin-HABP was not uniform depending on the molecular weight of HA. Further, the concentration of HABP to be immobilized or biotin-HABP and the composition of the buffer to be used in each step could regulate the degree of the difference in the reactivity depending on the molecular weight of HA (herein after referred to as the dependence on the molecular weight of HA).

Example 6
Test 1 for Condition of Additives on Reactivity of Biotin-HABP

To test the condition of additives on the reactivity of biotin-HABP, samples B (HA-964) and J (HA-22) were used to carry out the reaction and measurement in the same manner as that in Example 5 except the following conditions. The results are shown in Tables 8 and 9.

HABP immobilization concentration: 300 and 3,000 ng/mL

Buffer at the time of the HABP immobilization: PBS

Buffer in which HA standard is dissolved: ELISA basic buffer

Biotin-HABP concentration: 200 and 800 ng/mL

Addition concentration of guanidine hydrochloride to biotin-HABP solution: 0, 0.4, 0.6, 0.8, 1.0, 1.2, and 1.4 M HRP-avidin concentration: 500 ng/mL Coloring solution: 0.25 mg/mL OPD

TABLE 8

| | Reaction condition | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| HABP immobilization concentration (ng/mL) | 300 | 300 | 300 | 300 | 300 | 300 | 300 | 300 | 300 | 300 | 300 | 300 | 300 | 300 |
| Biotin-HABP concentration (ng/mL) | 200 | 200 | 200 | 200 | 200 | 200 | 200 | 800 | 800 | 800 | 800 | 800 | 800 | 800 |
| Concentration of guanidine hydrochloride added to biotin-HABP solution (M) | 0 | 0.4 | 0.6 | 0.8 | 1.0 | 1.2 | 1.4 | 0 | 0.4 | 0.6 | 0.8 | 1.0 | 1.2 | 1.4 |

An HA standard solution was tested without additives.

| | Reaction proportion of HA's having various molecular weights | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Absorbance of blank | 0.483 | 0.220 | 0.116 | 0.069 | 0.046 | 0.035 | 0.015 | 1.039 | 0.459 | 0.282 | 0.181 | 0.136 | 0.109 | 0.090 |
| HA-22·Absorbance of HA-22 at concentration of 1,000 ng/mL | 1.273 | 1.084 | 0.720 | 0.472 | 0.282 | 0.105 | 0.030 | 2.161 | 1.832 | 1.557 | 1.206 | 0.726 | 0.436 | 0.218 |
| HA-964·Absorbance of HA-964 at concentration of 1,000 ng/mL | 1.609 | 1.708 | 1.490 | 1.238 | 0.916 | 0.508 | 0.156 | 2.290 | 2.284 | 2.249 | 2.139 | 1.977 | 1.643 | 1.154 |
| Absorbance ratio of HA-22 to HA-964 | 70% | 58% | 44% | 34% | 27% | 15% | 11% | 90% | 75% | 65% | 52% | 32% | 21% | 12% |

* Calculation was made with a value obtained by subtracting the absorbance of the blank.

TABLE 9

| | Reaction condition | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| HABP immobilization concentration (ng/mL) | 3,000 | 3,000 | 3,000 | 3,000 | 3,000 | 3,000 | 3,000 | 3,000 | 3,000 | 3,000 | 3,000 | 3,000 | 3,000 | 3,000 |
| Biotin-HABP concentration (ng/mL) | 200 | 200 | 200 | 200 | 200 | 200 | 200 | 800 | 800 | 800 | 800 | 800 | 800 | 800 |
| Concentration of guanidine hydrochloride added to biotin-HABP solution (M) | 0 | 0.4 | 0.6 | 0.8 | 1.0 | 1.2 | 1.4 | 0 | 0.4 | 0.6 | 0.8 | 1.0 | 1.2 | 1.4 |

An HA standard solution was tested without additives.

| | Reaction proportion of HA's having various molecular weights | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| Absorbance of blank | 0.522 | 0.326 | 0.173 | 0.085 | 0.057 | 0.032 | 0.012 | 1.257 | 0.686 | 0.516 | 0.286 | 0.154 | 0.108 | 0.142 |
| HA-22·Absorbance of HA-22 at concentration of 1,000 ng/mL | 1.296 | 1.182 | 0.913 | 0.647 | 0.389 | 0.178 | 0.044 | 2.224 | 2.061 | 1.862 | 1.508 | 0.989 | 0.618 | 0.359 |
| HA-964·Absorbance of HA-964 at concentration of 1,000 ng/mL | 1.651 | 1.570 | 1.451 | 1.196 | 0.850 | 0.511 | 0.171 | 2.302 | 2.298 | 2.275 | 2.157 | 1.897 | 1.566 | 1.038 |
| Absorbance ratio of HA-22 to HA-964 | 69% | 69% | 58% | 51% | 42% | 30% | 20% | 93% | 85% | 77% | 65% | 48% | 35% | 24% |

* Calculation was made with a value obtained by subtracting the absorbance of the blank.

The above results revealed that, for example, the dependence on the molecular weight of HA could be regulated by adding guanidine hydrochloride to a buffer for dissolving biotin-HABP and changing the concentration of guanidine hydrochloride.

Example 7

Test for Adjustment of Coloring Strength

Figure 4:
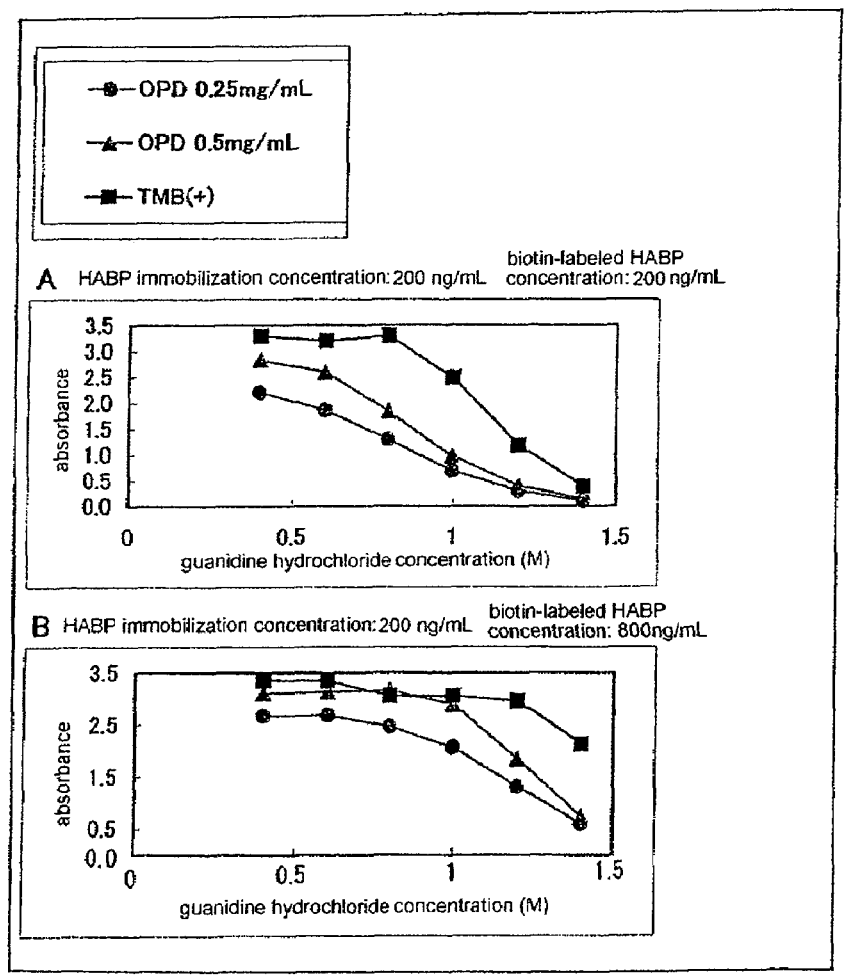
FIG. 4 are graphs showing results in which reactions with labeled HABPs were performed with change of coloring substances.

To test the adjustment of coloring strength, sample B (HA-964) was used to carry out the reaction and measurement in the same manner as that in Example 5 except the following conditions. The results are shown in FIG. 4.
  HABP immobilization concentration: 300 ng/mL
  Buffer at the time of the HABP immobilization: PBS
  Buffer in which HA standard is dissolved: ELISA basic buffer
  Biotin-HABP concentration: 200 and 800 ng/mL
  Addition concentration of guanidine hydrochloride to biotin-HABP solution: 0.4, 0.6, 0.8, 1.0, 1.2, and 1.4 M
  HRP-avidin concentration: 500 ng/mL
  Coloring solution: 0.25 mg/mL OPD, 0.5 mg/mL OPD and TMB (+) (100 μl as a reagent amount)

As a result, it was confirmed that the maximum absorbance in each condition for which the comparing investigation was conducted in Example 6 could be regulated by changing the concentration of HRP-avidin and the kind and concentration of the coloring substrate.

Example 8

Test 2 for Condition of Additives on Reactivity of Biotin-HABP

Figure 5:
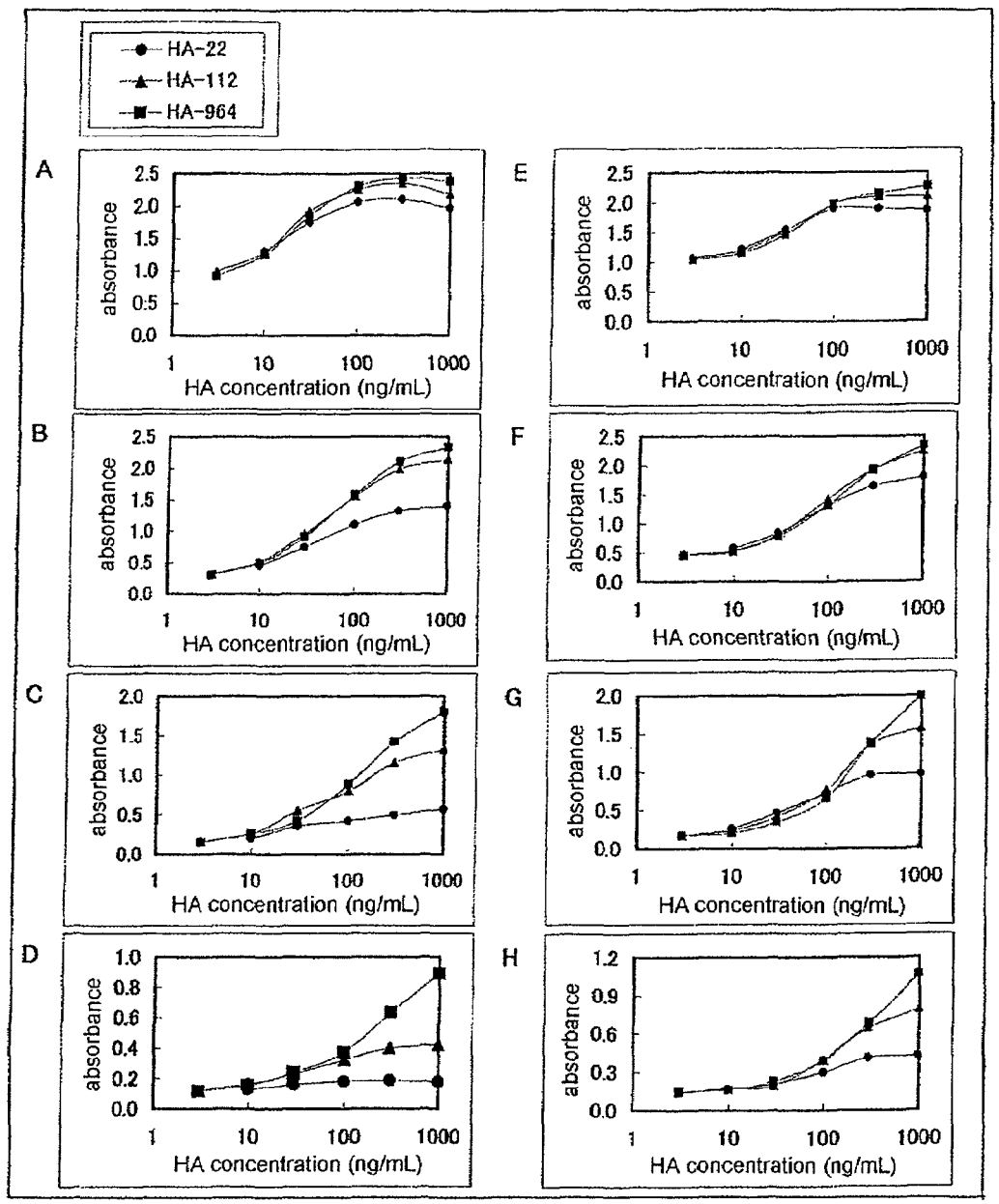
FIG. 5 are graphs showing results of tests for conditions of guanidine hydrochloride on biotin-HABP reactivity.

To test the condition of additives on the reactivity of biotin-HABP, sample B (HA-964), H (HA-112), and J (HA-22) were used to carry out the reaction and measurement in the same manner as that in Example 5 except the following conditions. The reaction conditions and the results are shown in Table 10 and FIG. 5, respectively.
  HABP immobilization concentration: 300 and 3,000 ng/mL
  Buffer at the time of the HABP immobilization: PBS
  Buffer in which HA standard is dissolved: ELISA basic buffer
  Biotin-HABP concentration: 200 ng/mL
  Addition concentration of guanidine hydrochloride to biotin-HABP solution: 0, 0.4, 0.8, and 1.2 M
  HRP-avidin concentration: 500 ng/mL
  Coloring solution: 0.25 mg/mL OPD, 0.5 mg/mL OPD and TMB (+) (100 μl as a reagent amount)

Consequently, the result was obtained that higher concentration of guanidine hydrochloride contributed to more significant dependence on the molecular weight. This result was consistent with the tendency obtained in Example 6. It was revealed that the combination of the regulation of the concentration, which was found in Example 6, of guanidine hydrochloride to be added to the biotin-labeled HABP solution, and the optimization of the coloring condition that was performed in Example 7, as shown in the present Example, allowed the construction of the reaction system exhibiting a variety of dependences on the molecular weight within a practical range of the maximum absorbance of 0.5 to 3.0.

It should be noted that, in Example 9 and other Examples with the numbers following 9 as well, similarly to this Example, the investigation on the coloring strength in the same manner as that in Example 7 was performed in advance as required, an appropriate condition was selected for the concentration of HRP-avidin and the kind and concentration of the coloring substrate, following which each test was performed.

Example 9

Test 3 for Condition of Additives on Reactivity of Biotin-HABP

Figure 6:
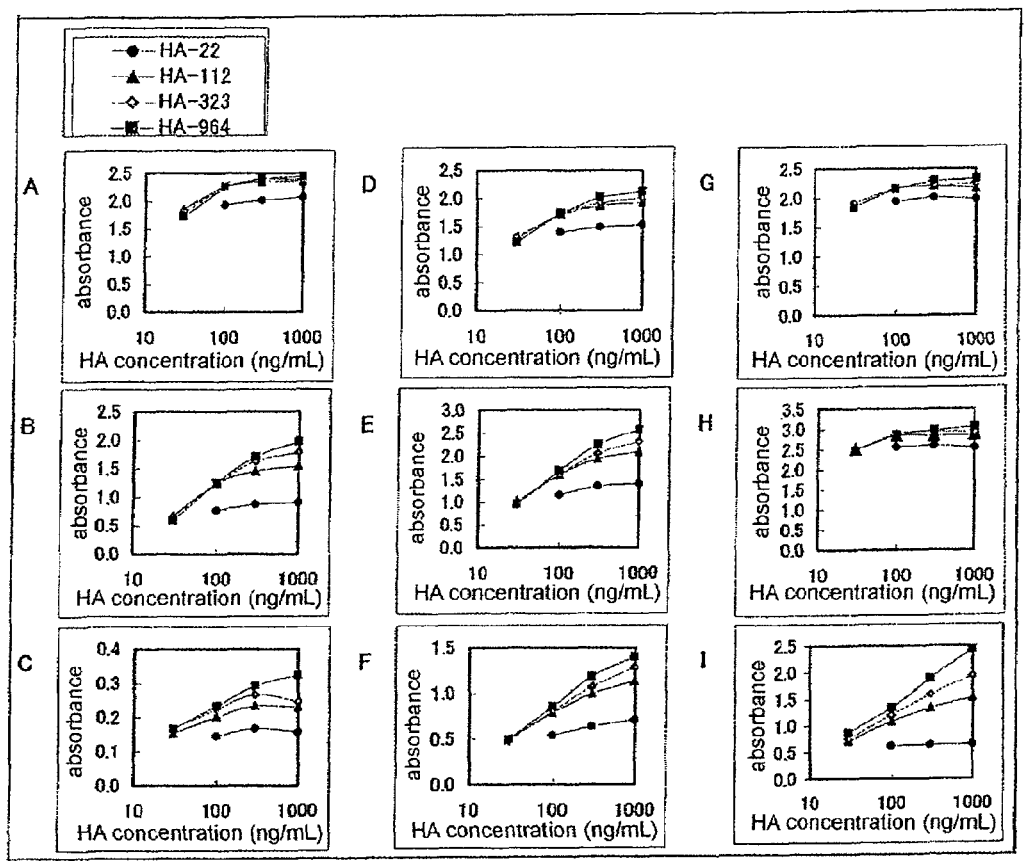
FIG. 6 are graphs showing results of tests for influences of a variety of additives on biotin-HABP reactivity.

To test the condition of additives on the reactivity of biotin-HABP, samples B (HA-964), E (HA-323), H (HA-112), and J (HA-22) were used to carry out the reaction and measurement in the same manner as that in Example 5 except the following conditions. The reaction conditions and the results are shown in Table 11 and FIG. 6, respectively.
  HABP immobilization concentration: 300 ng/mL
  Buffer at the time of the HABP immobilization: PBS
  Buffer in which HA standard is dissolved: ELISA basic buffer
  Biotin-HABP concentration: 200 ng/mL
  Kind and concentration of additives added to biotin-HABP solution
  1) Urea: 2.67 M, 5.33 M, and 8.0 M
  2) CS—C: 0.2 mg/mL, 1.0 mg/mL, and 10 mg/mL
  3) SDS: 0.025%, 0.05%, and 0.1%
  HRP-avidin concentration: 500 ng/mL
  Coloring solution: 0.25 mg/mL OPD, 0.5 mg/mL OPD and TMB (+) (100 μl as a reagent amount)

TABLE 10

| | Reaction conditions | | | | | | | |
|---|---|---|---|---|---|---|---|---|
| | A | B | C | D | E | F | G | H |
| HABP immobilization concentration (ng/mL) | 300 | 300 | 300 | 300 | 3,000 | 3,000 | 3,000 | 3,000 |
| Biotin-HABP concentration (ng/mL) | 200 | 200 | 200 | 200 | 200 | 200 | 200 | 200 |
| Addition concentration of guanidine hydrochloride to biotin-HABP solution (M) | 0 | 0.4 | 0.8 | 1.2 | 0 | 0.4 | 0.8 | 1.2 |
| HRP-avidin concentration (ng/mL) | 500 | 500 | 500 | 500 | 500 | 500 | 500 | 500 |
| Coloring substrate | OPD | OPD | OPD | TMB (+) | OPD | OPD | OPD | TMB (+) |
| Coloring substrate concentration (mg/mL) | 0.25 | 0.25 | 0.5 | 100 | 0.25 | 0.25 | 0.5 | 100 |

The numerical value of the coloring substrate concentration for TMB (+) represents the addition amount (μl) of the reagent.

TABLE 11

| Performance condition | Reaction condition | | | | | | | | |
|---|---|---|---|---|---|---|---|---|---|
| | A | B | C | D | E | F | G | H | I |
| HABP immobilization concentration (ng/mL) | 300 | 300 | 300 | 300 | 300 | 300 | 300 | 300 | 300 |
| Biotin-HABP concentration (ng/mL) | 200 | 200 | 200 | 200 | 200 | 200 | 200 | 200 | 200 |
| Kind of additives added to biotin-HABP solution | Urea | Urea | Urea | CS-C | CS-C | CS-C | SDS | SDS | SDS |
| Addition concentration of additives added to biotin-HABP solution | 2.67 | 5.33 | 8 | 0.2 | 1 | 10 | 0.025 | 0.05 | 0.1 |
| (Unit for addition concentration) | | (M) | | | (mg/mL) | | | (%) | |
| HRP-avidin concentration (ng/mL) | 500 | 500 | 500 | 500 | 500 | 500 | 500 | 500 | 500 |
| Coloring substrate | OPD | OPD | TMB (+) | OPD | OPD | TMB (+) | OPD | OPD | TMB (+) |
| Coloring substrate concentration (mg/mL) | 0.25 | 0.5 | 100 | 0.25 | 0.5 | 100 | 0.25 | 0.5 | 100 |

The numerical value of the coloring substrate concentration for TMB (+) represents the addition amount (μl) of the reagent.

As a result, it was revealed that, as the additives to a solution for dissolving biotin-HABP, in addition to guanidine hydrochloride, urea, SDS, CS-C, and the like could be utilized.

Example 10

Test for Biotin-HABP Concentration

Figure 7:
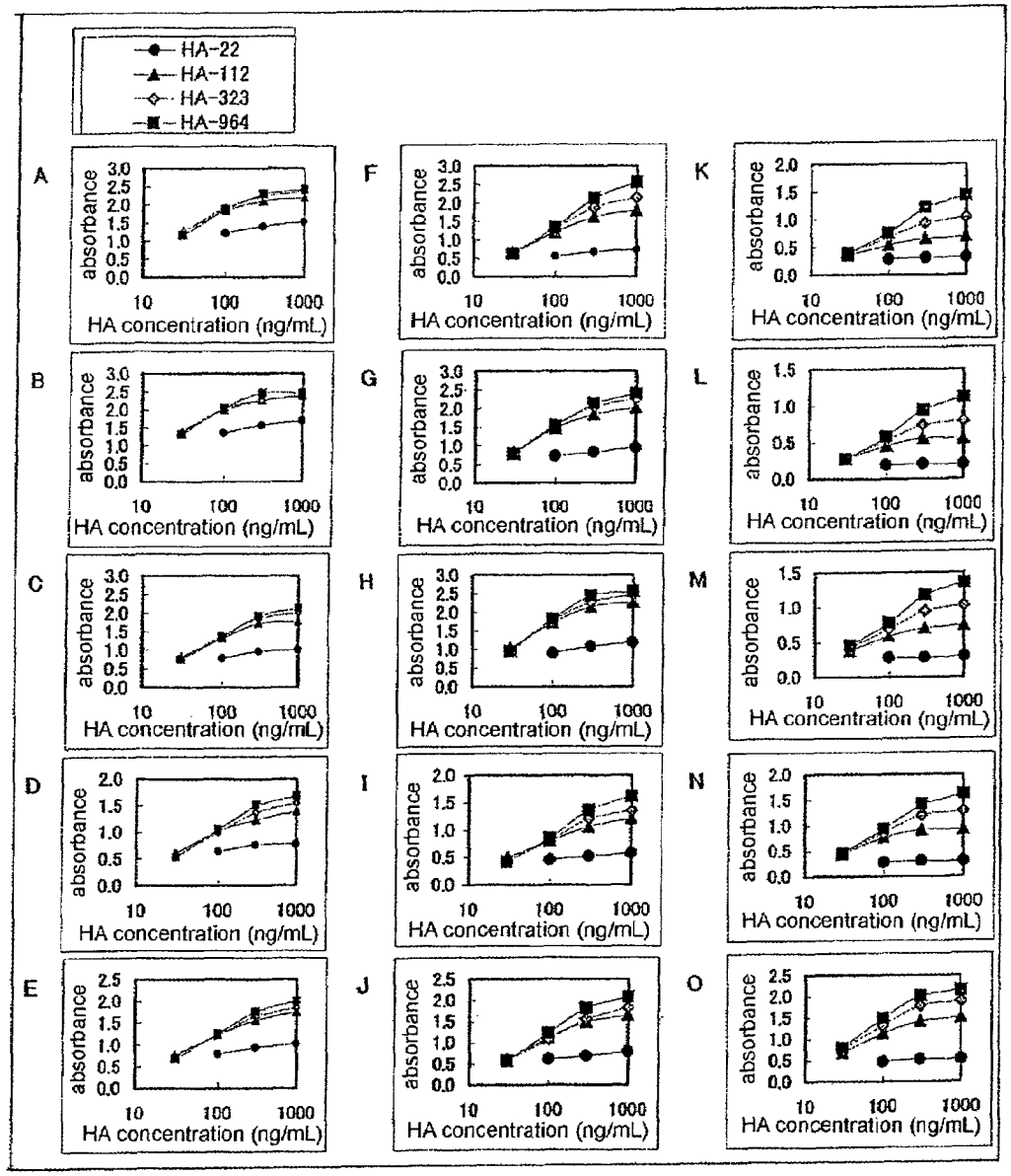
FIG. 7 are graphs showing results of tests performed in order to test an appropriate range of concentrations of biotin-HABP.

To test an appropriate range of the concentration of biotin-HABP, samples B (HA-964), E (HA-323), H (HA-112), and J (HA-22) were used to perform the reaction and measurement in the same manner as that in Example 5 except for the following condition. The reaction conditions, the results, and the ratios between the absorbances obtained in each sample calculated from the results are shown in Table 12, FIG. 7, and Table 13, respectively.

HABP immobilization concentration: 300 ng/mL
Buffer at the time of the HABP immobilization: PBS
Buffer in which HA standard is dissolved: ELISA basic buffer
Biotin-HABP concentration: 200, 400, 800, 1,600 and 3,200 ng/mL
Addition concentration of guanidine hydrochloride to biotin-HABP solution: 0.4, 0.8, and 1.2 M
HRP-avidin concentration: 100 and 500 ng/mL
Kind and concentration of coloring solution:
1) ABTS: 0.4 mg/mL
2) OPD: 0.2, 0.25, and 0.5 mg/mL
3) TMB-BLUE (100 μl as a reagent amount)

TABLE 12

| | Reaction condition | | | | | | | | |
|---|---|---|---|---|---|---|---|---|---|
| | A | B | C | D | E | F | G | H | I |
| HABP immobilization concentration (ng/mL) | 300 | 300 | 300 | 300 | 300 | 300 | 300 | 300 | 300 |
| Biotin-HABP concentration (ng/mL) | 200 | 400 | 800 | 1,600 | 3,200 | 200 | 400 | 800 | 1,600 |
| Addition concentration of guanidine hydrochloride to biotin-HABP solution (M) | 0.4 | 0.4 | 0.4 | 0.4 | 0.4 | 0.8 | 0.8 | 0.8 | 0.8 |
| HRP-avidin concentration (ng/mL) | 500 | 100 | 500 | 100 | 100 | 500 | 500 | 100 | 500 |
| Coloring substrate | OPD | OPD | ABTS | ABTS | ABTS | OPD | OPD | OPD | ABTS |
| Coloring substrate concentration (mg/mL) | 0.25 | 0.2 | 0.4 | 0.4 | 0.4 | 0.5 | 0.25 | 0.2 | 0.4 |

| | J | K | L | M | N | O |
|---|---|---|---|---|---|---|
| HABP immobilization concentration (ng/mL) | 300 | 300 | 300 | 300 | 300 | 300 |
| Biotin-HABP concentration (ng/mL) | 3,200 | 200 | 400 | 800 | 1,600 | 3,200 |

TABLE 12-continued

| | | | | | | |
|---|---|---|---|---|---|---|
| Addition concentration of guanidine hydrochloride to biotin-HABP solution (M) | 0.8 | 1.2 | 1.2 | 1.2 | 1.2 | 1.2 |
| HRP-avidin concentration (ng/mL) | 500 | 500 | 500 | 500 | 100 | 100 |
| Coloring substrate | ABTS | TMB-BLUE | OPD | OPD | OPD | OPD |
| Coloring substrate concentration (mg/mL) | 0.4 | 100 | 0.5 | 0.25 | 0.25 | 0.2 |

The numerical value of the coloring substrate concentration for TMB (+) represents the addition amount (μl) of the reagent.

TABLE 13

Reaction proportion of HA's having various molecular weights

| | A | B | C | D | E | F | G | H | I | J | K | L | M | N | O |
|---|---|---|---|---|---|---|---|---|---|---|---|---|---|---|---|
| Absorbance of blank | 0.326 | 0.339 | 0.285 | 0.245 | 0.298 | 0.102 | 0.146 | 0.210 | 0.197 | 0.226 | 0.163 | 0.103 | 0.135 | 0.124 | 0.198 |
| Absorbance ratio of HA-22 to HA-964 (HA concentration of 300 ng/mL) | 55% | 58% | 42% | 41% | 44% | 28% | 34% | 39% | 28% | 29% | 14% | 12% | 14% | 14% | 18% |
| Absorbance ratio of HA-112 to HA-964 (HA concentration of 300 ng/mL) | 90% | 90% | 88% | 78% | 87% | 75% | 85% | 87% | 74% | 79% | 46% | 54% | 54% | 61% | 67% |
| Absorbance ratio of HA-323 to HA-964 (HA concentration of 300 ng/mL) | 96% | 90% | 95% | 89% | 93% | 87% | 95% | 93% | 86% | 84% | 73% | 75% | 78% | 83% | 87% |
| Absorbance ratio of HA-22 to HA-964 (HA concentration of 1,000 ng/mL) | 57% | 64% | 40% | 37% | 43% | 26% | 36% | 42% | 27% | 31% | 12% | 10% | 14% | 12% | 17% |
| Absorbance ratio of HA-112 to HA-964 (HA concentration of 1,000 ng/mL) | 89% | 96% | 81% | 80% | 85% | 69% | 83% | 88% | 72% | 77% | 42% | 45% | 50% | 54% | 67% |
| Absorbance ratio of HA-323 to HA-964 (HA concentration of 1,000 ng/mL) | 97% | 98% | 93% | 91% | 91% | 83% | 94% | 96% | 82% | 86% | 69% | 69% | 74% | 78% | 87% |

* Calculation was made with a value obtained by subtracting the absorbance of the blank.

Those results indicated that the concentration of biotin-HABP was applicable within the range of at least 200 to 3,200 ng/mL. Further, in particular, in the case where the concentration of guanidine hydrochloride added to the biotin-HABP solution is relatively high, the results were obtained that the dependence on the molecular weight decreased as the concentration of the biotin-HABP increased. The present Example revealed that the concentration of the biotin-HABP could also regulate the dependence on the molecular weight.

Example 11

Test for Use of Additives in HA Standard Solution

Figure 8:
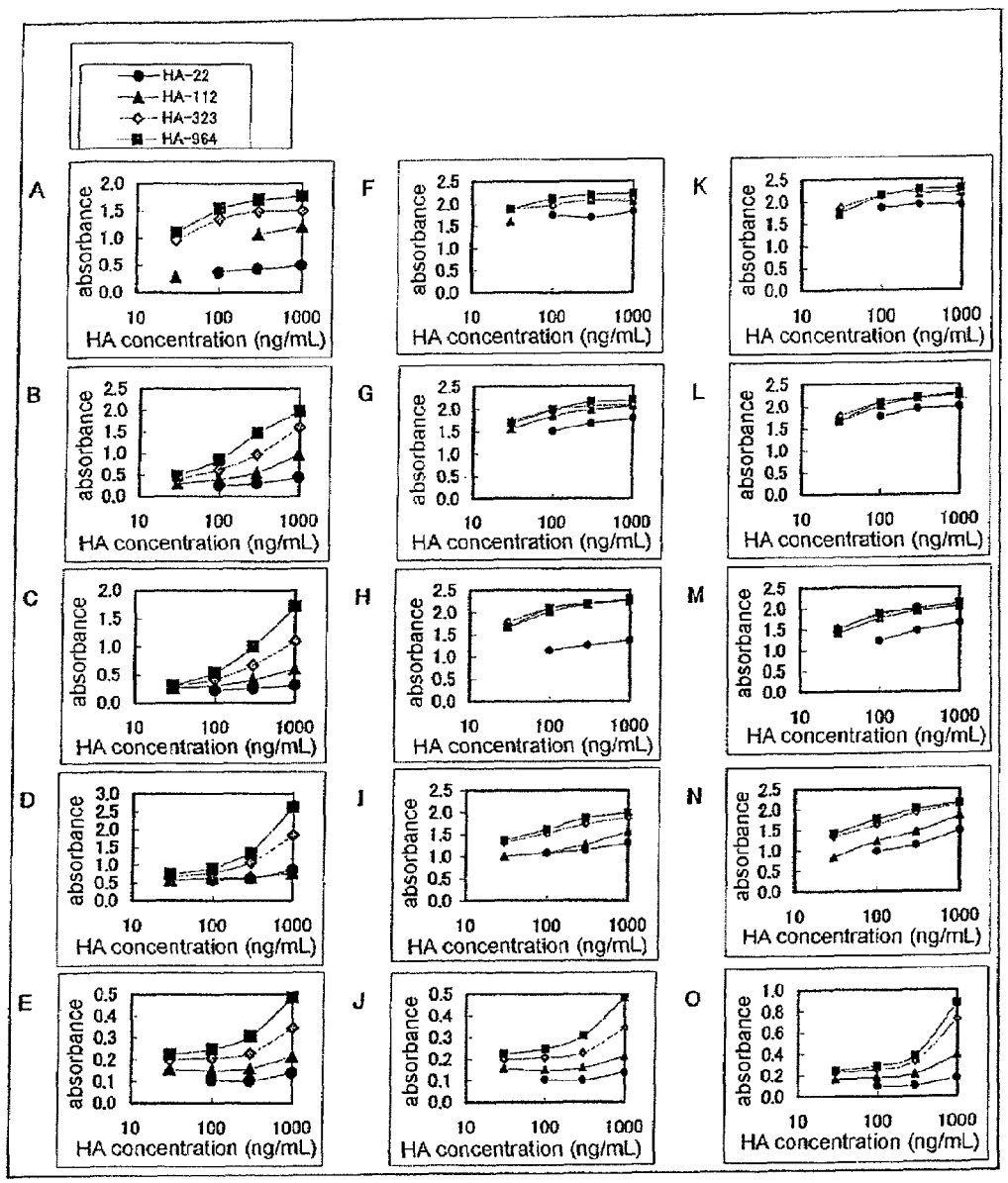
FIG. 8 are graphs showing results of tests for use of additives in HA standard solutions.

To test an influence when guanidine hydrochloride was used in an HA standard solution, samples B (HA-964), E (HA-323), H (HA-112), and J (HA-22) were used to perform the reaction and measurement in the same manner as that in Example 5 except for the following condition. The reaction conditions, the results, and the ratios between the absorbances obtained in each sample calculated from the results are shown in Table 14, FIG. 8, and Table 15, respectively.

HABP immobilization concentration: 30, 300, and 3,000 ng/mL
    Buffer at the time of the HABP immobilization: PBS
    Addition concentration of guanidine hydrochloride to HA standard solution: 0, 0.8, 1.2, 1.6, and 2.4 M
    Biotin-HABP concentration: 200 ng/mL
    Addition of guanidine hydrochloride to biotin-HABP solution: None
    HRP-avidin concentration: 100 and 500 ng/mL
    Kind and concentration of coloring solution:
    1) OPD: 0.25, 0.32, and 0.5 mg/mL
    2) TMB (+) (100 μl as a reagent amount)

TABLE 14

Reaction condition

| | A | B | C | D | E | F | G | H | I |
|---|---|---|---|---|---|---|---|---|---|
| HABP immobilization concentration (ng/mL) | 30 | 30 | 30 | 30 | 30 | 300 | 300 | 300 | 300 |
| Biotin-HABP concentration (ng/mL) | 200 | 200 | 200 | 200 | 200 | 200 | 200 | 200 | 200 |
| Addition concentration of guanidine hydrochloride to standard solution (M) | 0 | 0.8 | 1.2 | 1.6 | 2.4 | 0 | 0.8 | 1.2 | 1.6 |

TABLE 14-continued

| Reaction condition | | | | | | | | | |
|---|---|---|---|---|---|---|---|---|---|
| HRP-avidin concentration (ng/mL) | 500 | 100 | 500 | 100 | 100 | 500 | 500 | 100 | 500 |
| Coloring substrate | OPD | OPD | OPD | TMB+ | TMB+ | OPD | OPD | OPD | OPD |
| Coloring substrate concentration (mg/mL) | 0.25 | 0.32 | 0.5 | 100 | 100 | 0.25 | 0.25 | 0.25 | 0.25 |

| | J | K | L | M | N | O |
|---|---|---|---|---|---|---|
| HABP immobilization concentration (ng/mL) | 300 | 3,000 | 3,000 | 3,000 | 3,000 | 3,000 |
| Biotin-HABP concentration (ng/mL) | 200 | 200 | 200 | 200 | 200 | 200 |
| Addition concentration of guanidine hydrochloride to standard solution (M) | 2.4 | 0 | 0.8 | 1.2 | 1.6 | 2.4 |
| HRP-avidin concentration (ng/mL) | 500 | 500 | 500 | 500 | 100 | 100 |
| Coloring substrate | TMB+ | OPD | OPD | OPD | OPD | OPD |
| Coloring substrate concentration (mg/mL) | 100 | 0.25 | 0.25 | 0.25 | 0.25 | 0.5 |

The numerical value of the coloring substrate concentration for TMB (+) represents the addition amount (μl) of the reagent.

TABLE 15

| Reaction proportion of HA's having various molecular weights | | | | | | | | | | | | | | | |
|---|---|---|---|---|---|---|---|---|---|---|---|---|---|---|---|
| | A | B | C | D | E | F | G | H | I | J | K | L | M | N | O |
| Absorbance of blank | 0.164 | 0.214 | 0.221 | 0.572 | 0.086 | 0.746 | 1.017 | 0.950 | 1.033 | 0.123 | 0.404 | 0.683 | 0.692 | 0.743 | 0.090 |
| Absorbance ratio of HA-22 to HA-964 (HA concentration of 300 ng/mL) | 18% | 7% | 5% | 7% | 7% | 65% | 57% | 25% | 14% | −11% | 82% | 83% | 60% | 31% | 5% |
| Absorbance ratio of HA-112 to HA-964 (HA concentration of 300 ng/mL) | 59% | 27% | 25% | 10% | 33% | 91% | 84% | 98% | 29% | 20% | 95% | 99% | 95% | 56% | 41% |
| Absorbance ratio of HA-323 to HA-964 (HA concentration of 300 ng/mL) | 86% | 60% | 58% | 67% | 64% | 92% | 91% | 99% | 83% | 57% | 96% | 99% | 103% | 93% | 82% |
| Absorbance ratio of HA-22 to HA-964 (HA concentration of 1,000 ng/mL) | 21% | 13% | 6% | 14% | 13% | 73% | 65% | 31% | 29% | 4% | 80% | 81% | 68% | 53% | 11% |
| Absorbance ratio of HA-112 to HA-964 (HA concentration of 1,000 ng/mL) | 65% | 43% | 26% | 9% | 32% | 88% | 90% | 96% | 55% | 25% | 94% | 97% | 95% | 78% | 38% |
| Absorbance ratio of HA-323 to HA-964 (HA concentration of 1,000 ng/mL) | 84% | 79% | 59% | 62% | 65% | 93% | 92% | 99% | 89% | 61% | 96% | 99% | 97% | 98% | 81% |

In particular, the following result was obtained: in the range lower than 300 ng/mL at which the HABP immobilization concentration became saturated, higher concentration of guanidine hydrochloride added to the standard solution and the solution in which the test sample was dissolved resulted in more significant dependence on the molecular weight. The present Example revealed that the concentration of guanidine hydrochloride added to the standard solution and the buffer in which the test sample was dissolved could also regulate the dependence on the molecular weight.

Example 12

Test for Condition of Buffers at Time of HABP Immobilization

Figure 9:
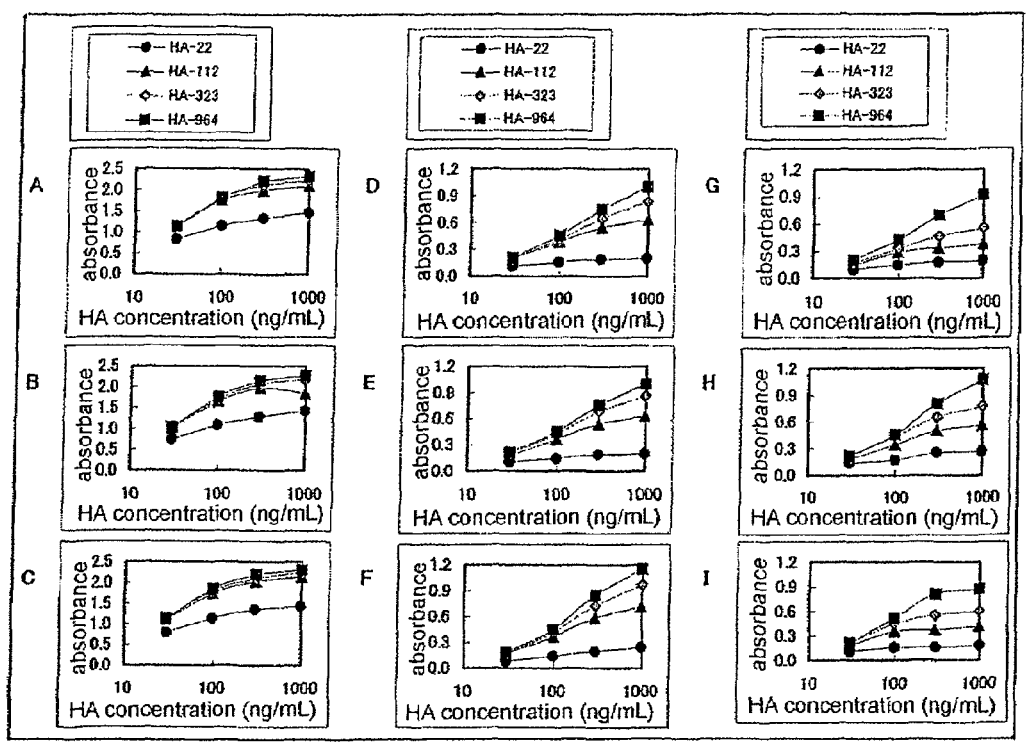
FIG. 9 are graphs showing results of tests for buffer conditions in the immobilization step of HABP.

To test condition of buffers at the time of HABP immobilization, the samples B (HA-964), E (HA-323), H (HA-112), and J (HA-22) were used to perform the reaction and measurement in the same manner as that in Example 5 except for the following condition. The reaction conditions, the results, and the ratios between the absorbances obtained in each sample calculated from the results are shown in Table 16, FIG. 9, and Table 17, respectively.

HABP immobilization concentration: 300 ng/mL

Buffer at the time of the HABP immobilization: PBS, 3 M NaCl-PBS, and 3.6 M NaCl-PBS Buffer in which HA standard is dissolved: ELISA basic buffer Biotin-HABP concentration: 200 ng/mL Addition concentration of guanidine hydrochloride to biotin-HABP solution: 0.4, 0.8, and 1.2 M HRP-avidin concentration: 500 ng/mL Concentration and concentration of coloring solution:
1) OPD: 0.25 mg/mL
2) OPD: 0.5 mg/mL and TMB (+) (100 μl as a reagent amount)

TABLE 16

| Reaction condition | A | B | C | D | E | F | G | H | I |
|---|---|---|---|---|---|---|---|---|---|
| HABP immobilization concentration (ng/mL) | 300 | 300 | 300 | 300 | 300 | 300 | 300 | 300 | 300 |
| Kind of additives added to PBS at time of HABP immobilization | None | NaCl | Guanidine hydrochloride | None | NaCl | Guanidine hydrochloride | None | NaCl | Guanidine hydrochloride |
| Concentration of additives added to PBS at time of HABP immobilization | | 3 M | 3.6 M | | 3 M | 3.6 M | | 3 M | 3.6 M |
| Biotin-HABP concentration (ng/mL) | 200 | 200 | 200 | 200 | 200 | 200 | 200 | 200 | 200 |
| Addition concentration of guanidine hydrochloride to biotin-HABP solution (M) | 0.4 | 0.4 | 0.4 | 0.8 | 0.8 | 0.8 | 1.2 | 1.2 | 1.2 |
| HRP-avidin concentration (ng/mL) | 500 | 500 | 500 | 500 | 500 | 500 | 500 | 500 | 500 |
| Coloring substrate | OPD | OPD | OPD | OPD | OPD | OPD | TMB (+) | TMB (+) | TMB (+) |
| Coloring substrate concentration (mg/mL) | 0.25 | 0.25 | 0.25 | 0.5 | 0.5 | 0.5 | 100 | 100 | 100 |

The numerical value of the coloring substrate concentration for TMB (+) represents the addition amount (μl) of the reagent.

TABLE 17

| Reaction proportion of HA's having various molecular weights | A | B | C | D | E | F | G | H | I |
|---|---|---|---|---|---|---|---|---|---|
| Absorbance ratio of HA-22 to HA-964 (HA concentration of 100 ng/mL) | 63% | 62% | 61% | 34% | 33% | 32% | 35% | 37% | 30% |
| Absorbance ratio of HA-112 to HA-964 (HA concentration of 100 ng/mL) | 97% | 94% | 94% | 84% | 81% | 81% | 68% | 76% | 68% |
| Absorbance ratio of HA-323 to HA-964 (HA concentration of 100 ng/mL) | 102% | 97% | 98% | 96% | 94% | 93% | 84% | 96% | 87% |
| Absorbance ratio of HA-22 to HA-964 (HA concentration of 300 ng/mL) | 60% | 60% | 62% | 26% | 25% | 23% | 25% | 31% | 20% |
| Absorbance ratio of HA-112 to HA-964 (HA concentration of 300 ng/mL) | 90% | 92% | 92% | 73% | 71% | 68% | 48% | 62% | 46% |
| Absorbance ratio of HA-323 to HA-964 (HA concentration of 300 ng/mL) | 95% | 96% | 96% | 86% | 91% | 85% | 66% | 81% | 68% |
| Absorbance ratio of HA-22 to HA-964 (HA concentration of 1,000 ng/mL) | 63% | 63% | 62% | 20% | 20% | 21% | 21% | 25% | 21% |
| Absorbance ratio of HA-112 to HA-964 (HA concentration of 1,000 ng/mL) | 90% | 81% | 93% | 63% | 63% | 62% | 41% | 52% | 48% |
| Absorbance ratio of HA-323 to HA-964 (HA concentration of 1,000 ng/mL) | 95% | 95% | 98% | 83% | 86% | 84% | 61% | 72% | 69% |

* Calculation was made with each absorbance value as it was.

Those results indicated that a buffer used at the time of HABP immobilization to the plate was not limited to a specified condition, and at least all the buffer conditions proposed in this Example were applicable.

Example 13

Test 1 for HABP Concentration at Time of HABP Immobilization

Figure 10:
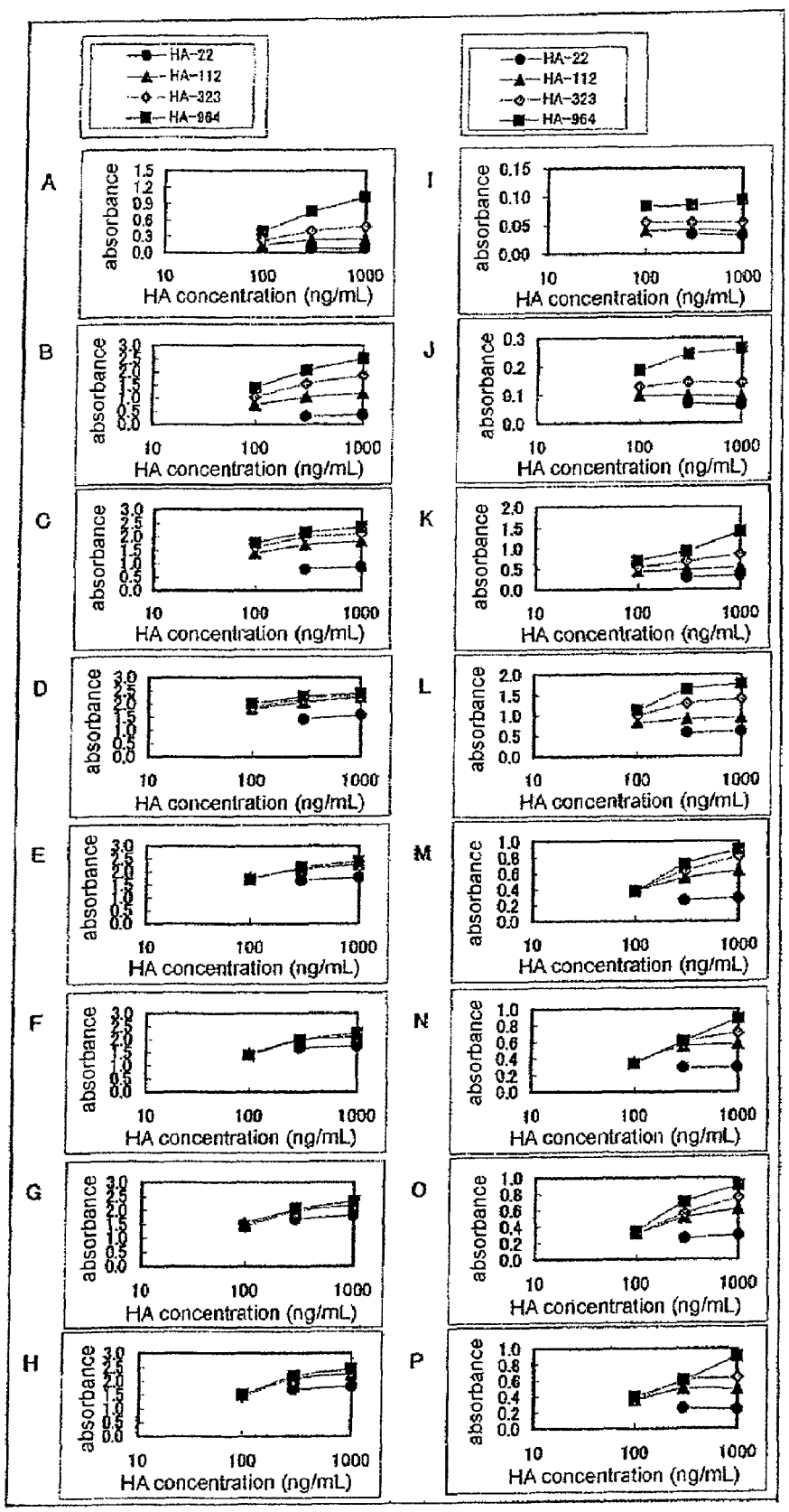
FIG. 10 are graphs showing results of tests for concentrations of HABP in the immobilization step of HABP.

To test HABP concentration at the time of HABP immobilization, samples B (HA-964), E (HA-323), H (HA-112), and J (HA-22) were used to perform the reaction and measurement in the same manner as that in Example 5 except for the following condition. The reaction conditions, the results, and the ratios between the absorbances obtained in each sample calculated from the results are shown in Table 18, FIG. 10, and Table 19, respectively.

HABP immobilization concentration: 10, 30, 100, 300, 1,000, 3,000, 10,000, and 30,000 ng/mL Buffer at the time of the HABP immobilization: PBS Buffer in which HA standard is dissolved: ELISA basic buffer Biotin-HABP concentration: 200 ng/mL Addition concentration of guanidine hydrochloride to biotin-HABP solution: 0.4 and 1.2 M HRP-avidin concentration: 500 ng/mL Kind and concentration of coloring solution:

1) OPD: 0.25 and 0.5 mg/mL

2) TMB (+) and TMB BLUE (100 μl as a reagent amount)

TABLE 18

| | Reaction condition | | | | | | | |
|---|---|---|---|---|---|---|---|---|
| | A | B | C | D | E | F | G | H |
| HABP immobilization concentration (ng/mL) | 10 | 30 | 100 | 300 | 1,000 | 3,000 | 10,000 | 30,000 |
| Biotin-HABP concentration (ng/mL) | 200 | 200 | 200 | 200 | 200 | 200 | 200 | 200 |
| Addition concentration of guanidine hydrochloride to biotin-HABP solution (M) | 0.4 | 0.4 | 0.4 | 0.4 | 0.4 | 0.4 | 0.4 | 0.4 |
| HRP-avidin concentration (ng/mL) | 500 | 500 | 500 | 500 | 500 | 500 | 500 | 500 |
| Coloring substrate | OPD | OPD | OPD | OPD | OPD | OPD | OPD | OPD |
| Coloring substrate concentration (mg/mL) | 0.5 | 0.5 | 0.25 | 0.25 | 0.25 | 0.25 | 0.25 | 0.25 |

| | I | J | K | L | M | N | O | P |
|---|---|---|---|---|---|---|---|---|
| HABP immobilization concentration (ng/mL) | 10 | 30 | 100 | 300 | 1,000 | 3,000 | 10,000 | 30,000 |
| Biotin-HABP concentration (ng/mL) | 200 | 200 | 200 | 200 | 200 | 200 | 200 | 200 |
| Addition concentration of guanidine hydrochloride to biotin-HABP solution (M) | 1.2 | 1.2 | 1.2 | 1.2 | 1.2 | 1.2 | 1.2 | 1.2 |
| HRP-avidin concentration (ng/mL) | 500 | 500 | 500 | 500 | 500 | 500 | 500 | 500 |
| Coloring substrate | TMB-BLUE | TMB-BLUE | TMB-BLUE | TMB-BLUE | TMB (+) | TMB (+) | TMB (+) | TMB (+) |
| Coloring substrate concentration (mg/mL) | 100 | 100 | 100 | 100 | 100 | 100 | 100 | 100 |

The numerical value of the coloring substrate concentration for TMB (+) represents the addition amount (μl) of the reagent.

TABLE 19

| | Reaction proportion of HA's having various molecular weights | | | | | | | | | | | | | | | |
|---|---|---|---|---|---|---|---|---|---|---|---|---|---|---|---|---|
| | A | B | C | D | E | F | G | H | I | J | K | L | M | N | O | P |
| Absorbance of blank | 0.032 | 0.114 | 0.242 | 0.304 | 0.424 | 0.444 | 0.445 | 0.397 | 0.03 | 0.06 | 0.238 | 0.419 | 0.122 | 0.129 | 0.125 | 0.126 |
| Absorbance ratio of HA-22 to HA-964 (HA concentration of 300 ng/mL) | 5% | 10% | 29% | 57% | 71% | 79% | 77% | 73% | 8% | 6% | 7% | 13% | 24% | 34% | 24% | 26% |
| Absorbance ratio of HA-112 to HA-964 (HA concentration of 300 ng/mL) | 28% | 47% | 76% | 89% | 95% | 100% | 96% | 94% | 23% | 21% | 36% | 41% | 71% | 87% | 67% | 77% |
| Absorbance ratio of HA-323 to HA-964 (HA concentration of 300 ng/mL) | 50% | 73% | 91% | 95% | 97% | 100% | 94% | 96% | 46% | 46% | 64% | 72% | 86% | 97% | 76% | 99% |
| Absorbance ratio of HA-22 to HA-964 (HA concentration of 1,000 ng/mL) | 5% | 10% | 31% | 61% | 69% | 73% | 73% | 69% | 3% | 3% | 9% | 14% | 22% | 22% | 22% | 15% |
| Absorbance ratio of HA-112 to HA-964 (HA concentration of 1,000 ng/mL) | 23% | 45% | 76% | 93% | 94% | 93% | 92% | 91% | 14% | 18% | 26% | 39% | 66% | 59% | 63% | 48% |
| Absorbance ratio of HA-323 to HA-964 (HA concentration of 1,000 ng/mL) | 45% | 73% | 89% | 97% | 97% | 94% | 94% | 92% | 39% | 41% | 52% | 73% | 89% | 77% | 81% | 66% |

* Calculation was made with a value obtained by subtracting the absorbance of the blank.

Those results indicated that, as the immobilization concentration of HABP, the concentration ranging from at least 10 to 30,000 ng/mL was applicable. Further, the result was obtained that the lower concentration of HABP contributed to the more significant dependence on the molecular weight within the range of less than 300 ng/mL at which the immobilization concentration of HABP was saturated. This Example revealed that the immobilization concentration of HABP also allowed the dependence on the molecular weight to be regulated.

Example 14

Test 2 for HABP Concentration at Time of HABP Immobilization

Figure 11:
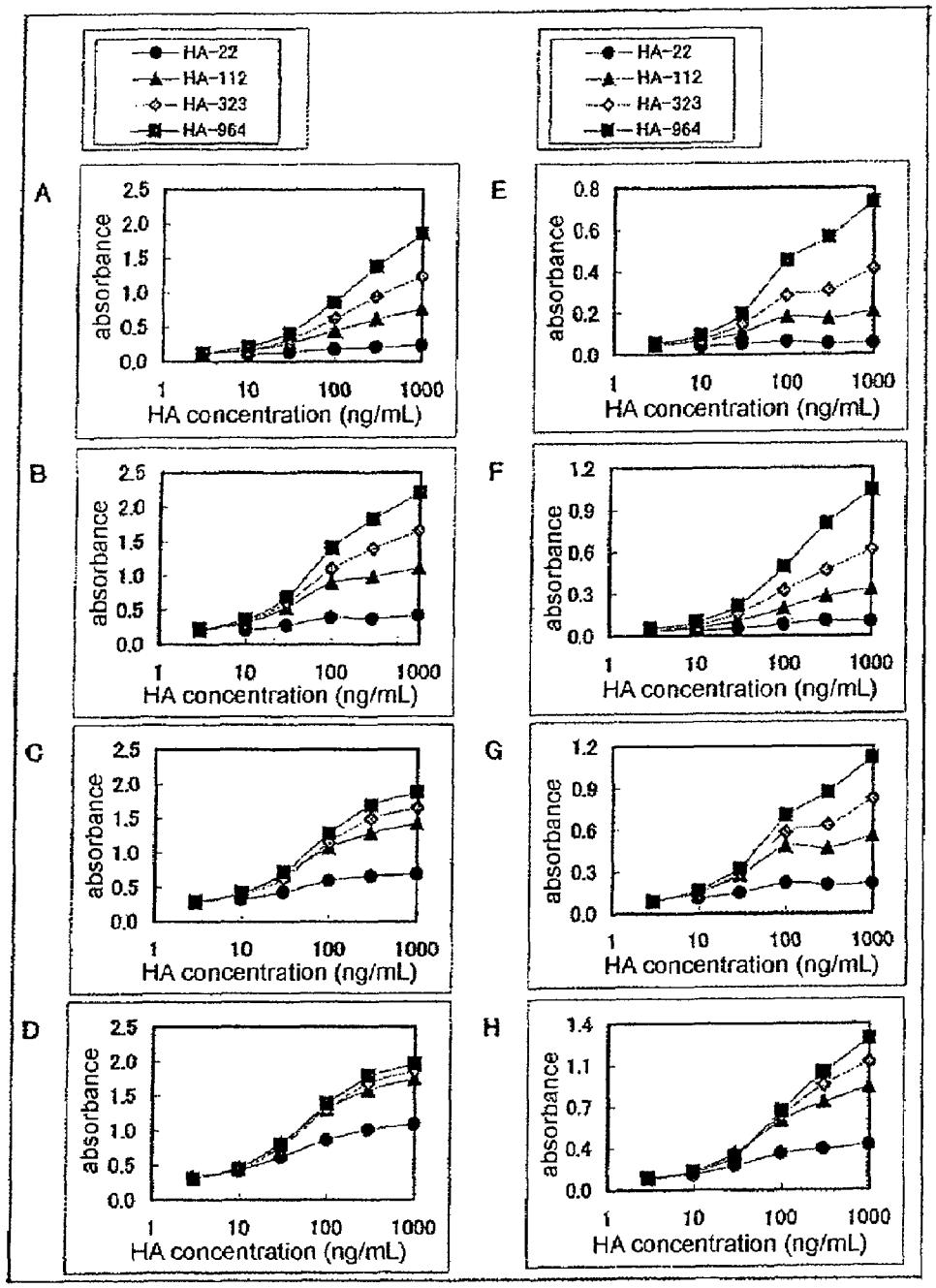
FIG. 11 are graphs showing results of tests for concentrations of HABP in the immobilization step of HABP.

To test HABP concentration at the time of the HABP immobilization, samples B (HA-964), E (HA-323), H (HA-112), and J (HA-22) were used to perform the reaction and measurement in the same manner as that in Example 13 except for the following condition. The reaction conditions, the results, and the ratios between the absorbances obtained in each sample calculated from the results are shown in Table 20, FIG. 11, and Table 21, respectively.

HABP immobilization concentration: 30, 60, 120, and 240 ng/mL
Addition concentration of guanidine hydrochloride to biotin-HABP solution: 0.4 and 0.8 M
HRP-avidin concentration: 500 ng/mL
Kind and concentration of coloring solution:
1) OPD: 0.25, and 0.5 mg/mL The results identical to those of Example 13 were obtained.

Example 15

Test for Combination of Conditions

To test whether the degree of dependence on the molecular weight can be regulated by the concentration of the various conditions investigated in Examples described above, samples B (HA-964), E (HA-323), H (HA-112), and J (HA-22) were used to perform the reaction and measurement in the same manner as that in Example 5 except for the following condition. The reaction conditions, the results, and the ratios between the absorbances obtained in each sample calculated from the results are shown in Table 22, FIG. 12, and Table 23, respectively.

HABP immobilization concentration: 100 ng/mL
Buffer at the time of the HABP immobilization: PBS
Addition concentration of guanidine hydrochloride to biotin-HABP solution: 0, 0.8, and 1.6 M

TABLE 20

| Reaction condition | | | | | | | | |
|---|---|---|---|---|---|---|---|---|
| | A | B | C | D | E | F | G | H |
| HABP immobilization concentration (ng/mL) | 30 | 60 | 120 | 240 | 30 | 60 | 120 | 240 |
| Biotin-HABP concentration (ng/mL) | 200 | 200 | 200 | 200 | 200 | 200 | 200 | 200 |
| Addition concentration of guanidine hydrochloride to biotin-HABP solution (M) | 0.4 | 0.4 | 0.4 | 0.4 | 0.8 | 0.8 | 0.8 | 0.8 |
| HRP-avidin concentration (ng/mL) | 500 | 500 | 500 | 500 | 500 | 500 | 500 | 500 |
| Coloring substrate | OPD | OPD | OPD | OPD | OPD | OPD | OPD | OPD |
| Coloring substrate concentration (mg/mL) | 0.5 | 0.5 | 0.25 | 0.25 | 0.25 | 0.25 | 0.25 | 0.25 |

TABLE 21

| Reaction proportion of HA's having various molecular weights | | | | | | | | |
|---|---|---|---|---|---|---|---|---|
| | A | B | C | D | E | F | G | H |
| Absorbance of blank | 0.078 | 0.139 | 0.200 | 0.244 | 0.030 | 0.029 | 0.060 | 0.075 |
| Absorbance ratio of HA-22 to HA-964 (HA density 100 ng/mL) | 9% | 15% | 29% | 46% | 5% | 10% | 18% | 33% |
| Absorbance ratio of HA-112 to HA-964 (HA density 100 ng/mL) | 45% | 57% | 79% | 92% | 34% | 35% | 62% | 84% |
| Absorbance ratio of HA-323 to HA-964 (HA density 100 ng/mL) | 69% | 75% | 87% | 91% | 59% | 63% | 79% | 92% |
| Absorbance ratio of HA-22 to HA-964 (HA density 300 ng/mL) | 10% | 14% | 31% | 50% | 4% | 11% | 18% | 30% |
| Absorbance ratio of HA-112 to HA-964 (HA density 300 ng/mL) | 41% | 50% | 73% | 87% | 27% | 33% | 50% | 73% |
| Absorbance ratio of HA-323 to HA-964 (HA density 300 ng/mL) | 66% | 75% | 87% | 93% | 52% | 57% | 71% | 88% |
| Absorbance ratio of HA-22 to HA-964 (HA density 1,000 ng/mL) | 9% | 14% | 29% | 49% | 4% | 7% | 15% | 25% |
| Absorbance ratio of HA-112 to HA-964 (HA density 1,000 ng/mL) | 38% | 47% | 73% | 87% | 25% | 30% | 47% | 66% |
| Absorbance ratio of HA-323 to HA-964 (HA density 1,000 ng/mL) | 65% | 73% | 86% | 94% | 55% | 58% | 72% | 83% |

\* Calculation was made with a value obtained by subtracting the absorbance of the blank.

Biotin-HABP concentration: 200 ng/mL
Addition concentration of guanidine hydrochloride to biotin-HABP solution: 0, 0.4, and 0.8 M
HRP-avidin concentration: 500 ng/mL
Kind and concentration of coloring solution:
1) OPD: 0.25, 0.32, and 0.5 mg/mL

TABLE 22

| Performance condition | Reaction condition | | | | | | | | |
|---|---|---|---|---|---|---|---|---|---|
| | A | B | C | D | E | F | G | H | I |
| HABP immobilization concentration (ng/mL) | 100 | 100 | 100 | 100 | 100 | 100 | 100 | 100 | 100 |
| Biotin-HABP concentration (ng/mL) | 200 | 200 | 200 | 200 | 200 | 200 | 200 | 200 | 200 |
| Concentration of guanidine hydrochloride added to HA standard solution (M) | 0 | 0.8 | 1.6 | 0 | 0.8 | 1.6 | 0 | 0.8 | 1.6 |
| Concentration of guanidine hydrochloride added to biotin-HABP solution (M) | 0 | 0 | 0 | 0.4 | 0.4 | 0.4 | 0.8 | 0.8 | 0.8 |
| HRP-avidin concentration (ng/mL) | 500 | 500 | 500 | 500 | 500 | 500 | 500 | 500 | 500 |
| Coloring substrate | OPD | OPD | OPD | OPD | OPD | OPD | OPD | OPD | OPD |
| Coloring substrate concentration (mg/mL) | 0.25 | 0.32 | 0.5 | 0.25 | 0.32 | 0.5 | 0.25 | 0.32 | 0.5 |

TABLE 23

| Reaction proportion of HA's having various molecular weights | | | | | | | | | |
|---|---|---|---|---|---|---|---|---|---|
| | A | B | C | D | E | F | G | H | I |
| Absorbance of blank | 0.529 | 0.437 | 0.153 | 0.172 | 0.215 | 0.247 | 0.094 | 0.083 | 0.093 |
| Absorbance ratio of HA-22 to HA-964 (HA density 100 ng/mL) | 38% | 2% | 3% | 14% | 14% | 2% | 12% | 8% | 40% |
| Absorbance ratio of HA-112 to HA-964 (HA density 100 ng/mL) | 82% | 39% | 36% | 61% | 55% | 42% | 54% | 40% | 9% |
| Absorbance ratio of HA-323 to HA-964 (HA density 100 ng/mL) | 90% | 68% | 63% | 77% | 76% | 53% | 72% | 66% | 42% |
| Absorbance ratio of HA-22 to HA-964 (HA density 300 ng/mL) | 38% | 4% | 8% | 16% | 14% | 10% | 11% | 0% | 0% |
| Absorbance ratio of HA-112 to HA-964 (HA density 300 ng/mL) | 85% | 46% | 30% | 64% | 51% | 43% | 48% | 17% | 9% |
| Absorbance ratio of HA-323 to HA-964 (HA density 300 ng/mL) | 93% | 77% | 57% | 79% | 71% | 58% | 68% | 58% | 38% |
| Absorbance ratio of HA-22 to HA-964 (HA density 1,000 ng/mL) | 38% | 7% | 11% | 18% | 16% | 8% | 11% | 7% | 0% |
| Absorbance ratio of HA-112 to HA-964 (HA density 1,000 ng/mL) | 85% | 58% | 35% | 63% | 58% | 33% | 45% | 19% | 12% |
| Absorbance ratio of HA-323 to HA-964 (HA density 1,000 ng/mL) | 92% | 84% | 59% | 79% | 77% | 46% | 68% | 60% | 44% |

* Calculation was made with a value obtained by subtracting the absorbance of the blank.

As apparent from this Example, the degree of the dependence on the molecular weight in the step (2) of the method of the present invention can be regulated with freedom by optimizing the combination of a plurality of conditions. In practice, the condition which is to be the optimum embodiment can be selected appropriately, in consideration of measurement sensitivity, measurement accuracy, stability, operativity, and the like, in setting the condition for the method and constructing the kit for measurement.

Example 16

Measurement 1 for Specimen

Hereinafter, there is given a specific example of the measurement of the molecular weight for the test sample.

As a test sample, there was used a sample obtained by adding 3 kinds of HA's, samples D (HA-606), G (HA-182), and I (HA-61), in which the molecular weight was measured in Example 1, to Dulbecco's modified Eagle's medium. As a standard sample in the step (1), sample J (HA-22) itself was used. As a standard sample in the step (2), samples B (HA-964), E (HA-323), H (HA-112), and J (HA-22) were used.

Those samples were appropriately diluted, respectively, and the step (1) was performed according to the method as described in Example 3. The results of the absorbance measurement for the standard sample are shown in Table 24 as described below, the values obtained by logarithmically converting the results together with the concentration values are shown in Table 25, and the results of the absorbance measurement for the test sample are shown in Table 26.

TABLE 24

| Absorbance of standard solution | |
|---|---|
| HA concentration (ng/mL) | Absorbance (492 nm) |
| 0 | 2.248 |
| 6.25 | 2.007 |
| 12.5 | 1.750 |
| 25 | 1.428 |
| 50 | 1.086 |

TABLE 24-continued

Absorbance of standard solution

| HA concentration (ng/mL) | Absorbance (492 nm) |
|---|---|
| 100 | 0.797 |
| 200 | 0.544 |
| 400 | 0.359 |

TABLE 25

Logarithmic conversion value of data for standard solution

| Logarithmic value of HA concentration | Logarithmic value of absorbance |
|---|---|
| 8.740 | 7.604 |
| 9.433 | 7.467 |
| 10.127 | 7.264 |
| 10.820 | 6.990 |
| 11.513 | 6.680 |
| 12.206 | 6.299 |
| 12.899 | 5.883 |

TABLE 26

Measurements for absorbance and HA concentration for test sample

| Sample | Absorbance (492 nm) | HA Concentration of test solution* (ng/mL) | Dilute strength of test solution (fold) | HA Concentration for sample stock solution (μg/mL) |
|---|---|---|---|---|
| Medium added with HA-61 | 1.089 | 48.7 | 200 | 9.74 |
| Medium added with HA-182 | 0.905 | 78.0 | 200 | 15.59 |
| Medium added with HA-606 | 1.066 | 51.6 | 200 | 10.31 |

Figure 13:
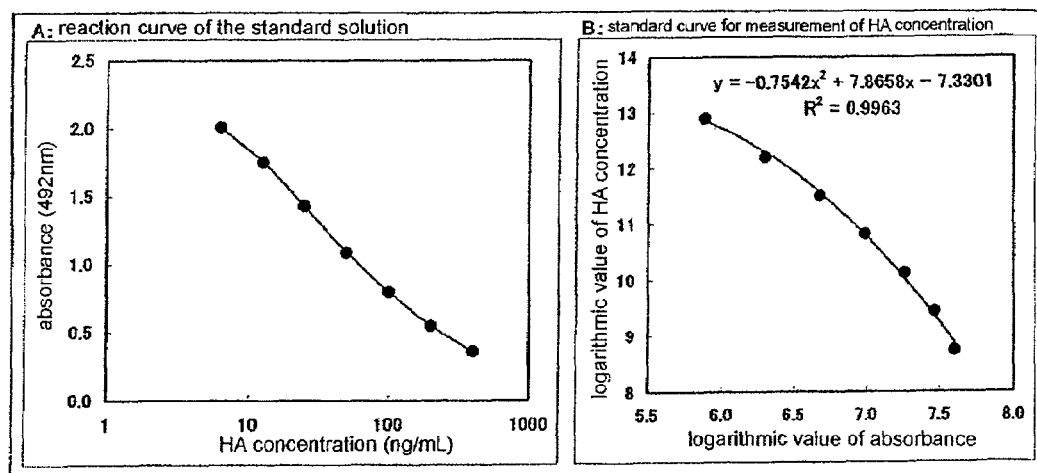
FIG. 13 are graphs each showing a reaction curve (A) of a standard solution for measurement of a concentration of HA in a sample and a standard curve (B) for measurement of a molecular weight of HA obtained from the curve (A).

*Calculation was made by substituting the logarithmic value of the absorbance of the test sample into x in the correlation equation in FIG. 13B.

On the basis of the absorbance data in the standard solution (FIG. 13A), the calibration curve as shown in FIG. 13B was prepared. The calibration curve was utilized to determine the concentration of HA in the sample. The results are shown in Table 26.

Figure 14:
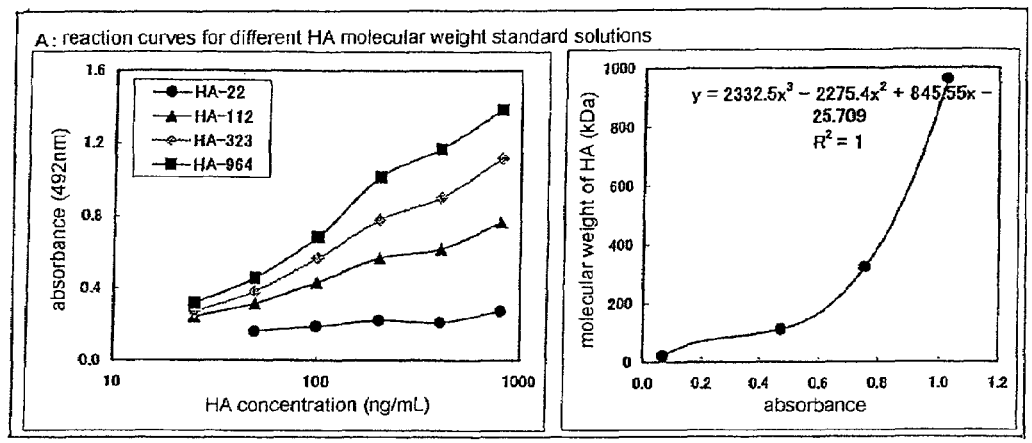
FIG. 14 are graphs each showing reaction curves (A) of the standard solutions for measurement of a molecular weight of HA in a sample and a standard curve (B) for determination of the molecular weight of HA obtained from the curves (A).

On the basis of those results, each of the test samples was diluted to a concentration of 400 ng/mL. The condition E in Example 15 was applied to perform the step (2). The results of obtained absorbance are shown in Table 28 as described below. Further, the standard samples with various concentrations were subjected to similar operation. The results of obtained absorbance are shown in Table 27 as described below. In FIG. 14A, there is given the reaction curve for each standard sample obtained from those values. Further, in FIG. 14B, there is given the standard curve obtained from the results obtained at a concentration of 400 ng/mL among those results.

An absorbance value of each sample having a concentration of 400 ng/mL and a standard curve in FIG. 14B was used to determine the molecular weight of HA in each test sample (step (3)). The results are shown in Table 28.

TABLE 27

Absorbance of standard solution for molecular weight measurement

| | Sample | | | | | Sample | | | |
|---|---|---|---|---|---|---|---|---|---|
| | J | H | E | B | | J | H | E | B |
| | Molecular weight (kDa) | | | | | Molecular weight (kDa) | | | |
| HA concentration (ng/mL) | 22 | 112 | 323 | 964 | HA concentration (ng/mL) | 22 | 112 | 323 | 964 |
| | Absorbance (492 nm) | | | | | Value obtained by subtracting blank | | | |
| 0 | 0.143 | | | | 0 | | | | |
| 25 | | 0.243 | 0.27 | 0.317 | 25 | | 0.101 | 0.127 | 0.175 |
| 50 | 0.161 | 0.316 | 0.383 | 0.457 | 50 | 0.019 | 0.173 | 0.241 | 0.315 |
| 100 | 0.189 | 0.432 | 0.566 | 0.685 | 100 | 0.047 | 0.289 | 0.423 | 0.542 |
| 200 | 0.223 | 0.568 | 0.78 | 1.016 | 200 | 0.08 | 0.425 | 0.638 | 0.873 |
| 400 | 0.211 | 0.616 | 0.9 | 1.168 | 400 | 0.068 | 0.473 | 0.758 | 1.026 |
| 800 | 0.272 | 0.765 | 0.116 | 1.384 | 800 | 0.13 | 0.622 | 0.974 | 1.242 |

TABLE 28

Measurements for absorbance and HA molecular weight for test sample

| Sample | HA concentration of test solution (ng/mL) | Absorbance (492 nm) | Value obtained by subtracting blank | HA molecular weight for sample stock solution (kDa) |
|---|---|---|---|---|
| Medium added with HA-61 | 400 | 0.395 | 0.253 | 80 |
| Medium added with HA-182 | 400 | 0.697 | 0.555 | 141 |
| Medium added with HA-606 | 400 | 0.968 | 0.826 | 434 |

*Calculation was made by substituting each absorbance (a value obtained by subtracting the blank) into x in the correlation equation in FIG. 14B.

Example 17

Measurement 2 for Specimen

Hereinafter, there is given another specific example of the measurement of the molecular weight for the test sample.

As the test sample, there was used a sample obtained by adding 3 kinds of HA's, samples D (HA-606), F (HA-248), and I (HA-61), in which the molecular weight was measured in Example 1, to Dulbecco's modified Eagle's medium. As a standard sample in the step (1), sample J (HA-22) itself was used. As a standard sample in the step (2), samples B (HA-964), E (HA-323), H (HA-112), and J (HA-22) were used.

Those samples were diluted respectively as appropriate. The step (1) was performed according to the method as described in Example 3, and, in parallel, the step (2) was performed by applying condition A of Example 14.

For the step (1), the results of the absorbance measurement for the standard sample was shown in Table 29 as described below, the logarithmic conversion values of the results together with the logarithmic conversion values of the concentration were shown in Table 30, and the results of the absorbance measurement for the test sample was shown in Table 31.

TABLE 29

Absorbance of standard solution

| HA concentration (ng/mL) | Absorbance (492 nm) |
|---|---|
| 0 | 2.318 |
| 6.25 | 2.071 |
| 12.5 | 1.861 |
| 25 | 1.496 |
| 50 | 1.148 |
| 100 | 0.859 |
| 200 | 0.621 |
| 400 | 0.444 |

TABLE 30

Logarithmic conversion value of data for standard solution

| Logarithmic value of HA concentration | Logarithmic value of absorbance |
|---|---|
| 8.74 | 7.636 |
| 9.433 | 7.529 |
| 10.127 | 7.311 |
| 10.82 | 7.046 |
| 11.513 | 6.755 |
| 12.206 | 6.431 |
| 12.899 | 6.096 |

TABLE 31

Measurements for absorbance and HA concentration of test sample

| Sample | Absorbance (492 nm) | HA concentration (ng/mL) |
|---|---|---|
| Medium added with HA-61 | 0.767 | 138 |
| Medium added with HA-248 | 0.581 | 243 |
| Medium added with HA-606 | 0.54 | 276 |

Figure 15:
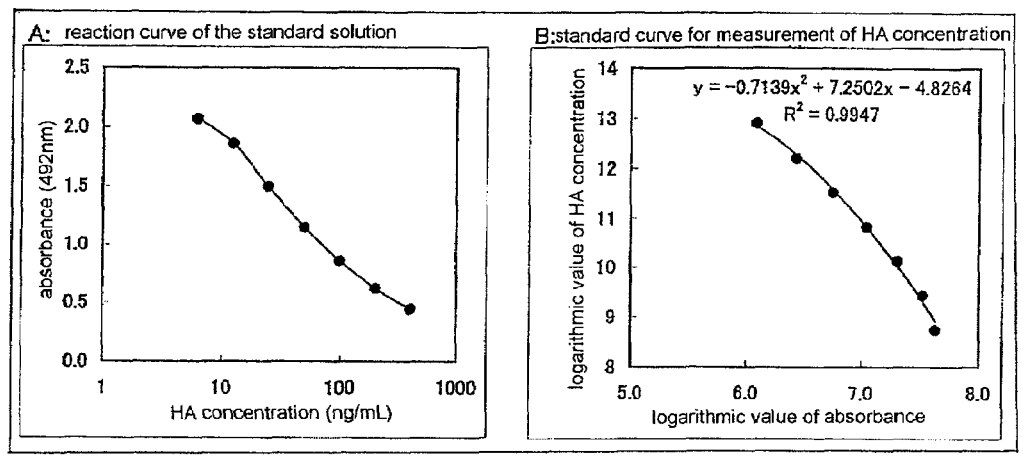
FIG. 15 are graphs each showing a reaction curve (A) of the standard solution for measurement of the concentration of HA in a sample and a standard curve (B) for determination of the molecular weight of HA obtained from the curve (A) together with an approximation equation.

On the basis of the absorbance data in the standard solution, the calibration curve as shown in FIG. 15A was prepared. The approximation equations of the calibration curves representing the absorbance and concentration in logarithmic values are shown in FIG. 15B. The calibration curve was utilized to determine the concentration of HA in the sample. The results were shown in Table 31.

Figure 16:
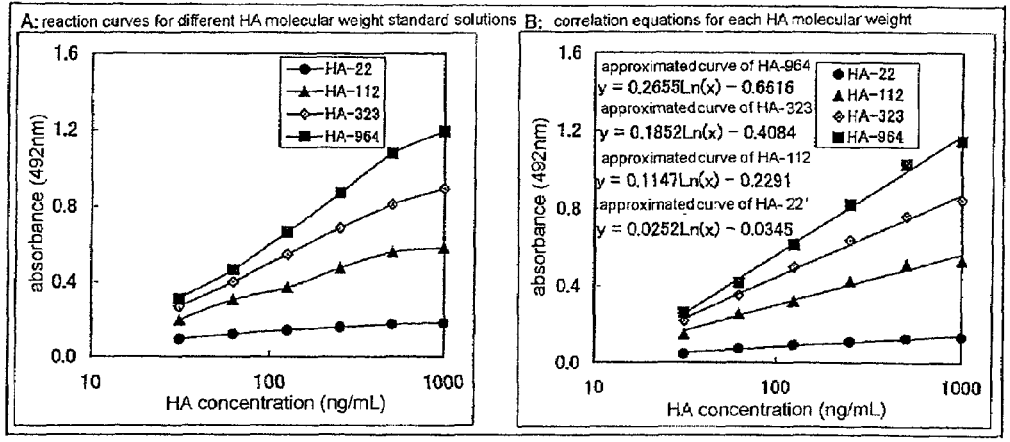
FIG. 16 are graphs each showing reaction curves (A) of the standard solutions for measurement of the molecular weight of HA in a sample and the standard curves (B) together with approximation equations expressed in logarithmic functions (B).

Further, the results of the absorbance for the standard sample obtained in the step (2) are shown in Table 32 described below. In FIG. 16A, there is given the reaction curve showing the absorbance of the concentration of HA for each standard sample obtained from those values. The results of the absorbance of the test sample are shown in Table 34.

Finally, on the basis of the results obtained in the steps (1) and (2), the calculation of the molecular weight, which was the step (3), was performed. First, in FIG. 16B, there is given the equation obtained by logarithmically approximating the reaction curve for each HA molecular weight standard sample obtained in the step (2). The absorbance value for each molecular weight standard sample at the concentration of HA in each test sample can be determined by substituting the concentration of HA for each test sample determined in the step (1) into x in those approximation equations. The values determined by this operation are shown in Table 33.

Figure 17:
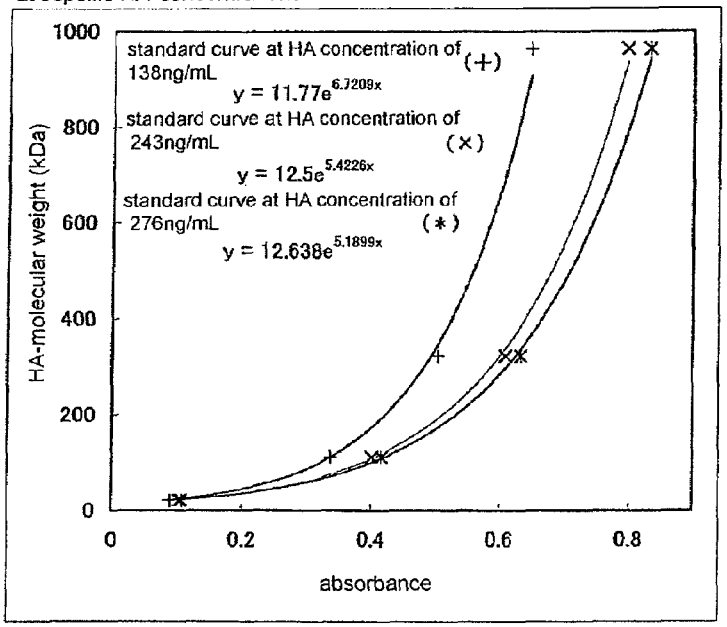
FIG. 17 is a graph showing standard curves for measurement of the molecular weight of HA in a sample together with approximation equations.

In addition, the absorbance value in Table 33 determined at the concentration of HA for each test sample and the molecular weight of HA are plotted on x- and y-axis, respectively, and the approximation equation for the resulting curve is determined, whereby the calibration curve for measurement of the molecular weight at the concentration of HA for each test sample can be prepared. In FIG. 17, there is given the approximation equation for thus obtained calibration curve for measurement of the molecular weight at each concentration. The molecular weight of HA in the test sample can be determined by substituting the absorbance value of the test sample determined in the step (2) into x in the equation corresponding to the concentration of each test sample in those approximation equations. Thus obtained molecular weights are shown in Table 34.

Like this Example, even if the steps (1) and (2) can be performed independently without the operation such as selecting the reaction condition in the step (2) on the basis of the results in the step (1), the molecular weight of HA can be determined as long as the absorbance value obtained for the test sample in each step falls within each measurement range.

TABLE 32

| A: Absorbances of standard solutions for different HA molecular weights | | | | | B: Absorbances of standard solutions for different HA molecular weights (value obtained by subtracting blank) | | | | |
|---|---|---|---|---|---|---|---|---|---|
| | Sample | | | | | Sample | | | |
| | J | H | E | B | | J | H | E | B |
| | Molecular weight (kDa) | | | | | Molecular weight (kDa) | | | |
| HA concentration (ng/mL) | 22 | 112 | 323 | 964 | HA concentration (ng/mL) | 22 | 112 | 323 | 964 |
| | Absorbance (492 nm) | | | | | Absorbance (value obtained by subtracting blank) | | | |
| 0 | 0.049 | | | | 0 | 0 | | | |
| 31.3 | 0.094 | 0.197 | 0.266 | 0.310 | 31.3 | 0.045 | 0.148 | 0.217 | 0.261 |
| 62.5 | 0.121 | 0.304 | 0.399 | 0.465 | 62.5 | 0.072 | 0.255 | 0.350 | 0.416 |
| 125 | 0.142 | 0.369 | 0.546 | 0.662 | 125 | 0.093 | 0.320 | 0.497 | 0.613 |
| 250 | 0.158 | 0.474 | 0.685 | 0.868 | 250 | 0.109 | 0.425 | 0.636 | 0.819 |
| 500 | 0.173 | 0.558 | 0.807 | 1.073 | 500 | 0.124 | 0.509 | 0.758 | 1.024 |
| 1,000 | 0.182 | 0.580 | 0.892 | 1.192 | 1,000 | 0.133 | 0.531 | 0.843 | 1.143 |

TABLE 33

Calculated absorbance values of standard solutions for different HA molecular weights at predetermined HA concentration

| | Molecular weight (kDa) | | | |
|---|---|---|---|---|
| | 22 | 112 | 323 | 964 |
| HA concentration (ng/mL) | Absorbance (Value obtained by subtracting blank) | | | |
| 138 | 0.09 | 0.336 | 0.504 | 0.647 |
| 243 | 0.104 | 0.401 | 0.609 | 0.796 |
| 276 | 0.107 | 0.416 | 0.633 | 0.831 |

TABLE 34

Measurement results of molecular weight for test sample

| Test sample | HA concentration (ng/mL) | Absorbance (492 nm) | Value obtained by subtracting blank | Calculated value of HA molecular weight (kDa) |
|---|---|---|---|---|
| Medium added with HA-61 | 138 | 0.247 | 0.198 | 45 |
| Medium added with HA-248 | 243 | 0.569 | 0.52 | 210 |
| Medium added with HA-606 | 276 | 0.779 | 0.73 | 559 |

TABLE 35

Examples of combinations of pretreatment steps

| Pretreatment step 1) Protease treatment | Pretreatment step 2) Deactivation treatment | Pretreatment step 3) Neutralization treatment | Pretreatment step 4) Correction treatment |
|---|---|---|---|
| Actinase | Trichloroacetic acid-Centrifugation | Tris | Addition of BSA-sodium chloride solution |
| Actinase | Trichloroacetic acid-Centrifugation | Desalting with desalting column, dialysis, and the like | Addition of BSA-Tris-sodium chloride solution |
| Collagenase | Trichloroacetic acid-Centrifugation | Tris | Addition of BSA-sodium chloride solution |
| Collagenase | EDTA, EGTA | None | Addition of BSA-Tris-sodium chloride solution |
| Papain | Trichloroacetic acid-Centrifugation | Tris | Addition of BSA-sodium chloride solution |
| Papain | Monoiodoacetic acid | Desalting with desalting column, dialysis, and the like | Addition of BSA-Tris-sodium chloride solution |
| Trypsin | Trichloroacetic acid-Centrifugation | Tris | Addition of BSA-sodium chloride solution |

TABLE 35-continued

Examples of combinations of pretreatment steps

| Pretreatment step 1) Protease treatment | Pretreatment step 2) Deactivation treatment | Pretreatment step 3) Neutralization treatment | Pretreatment step 4) Correction treatment |
|---|---|---|---|
| Trypsin | TPCK, TLCK, and soybean trypsin inhibitase | None | Addition of BSA-Tris-sodium chloride solution |

Example 18

Confirmation for Protease Deactivation Effect in Carrying Out Pretreatment Steps 2) and 3)

Actinase AF was dissolved in 0.135M NaCl-10 mM Tris-HCl (having a pH of 8.0) so as to achieve a concentration of 2% or 6% to afford a test sample solution. A part of the solution was dispensed, boiled for 10 minutes to cause the deactivation, resulting in a control solution A. Further, a buffer without actinase was taken to be a control solution B.

Each solution was cooled with ice. After that, a 40%, 12%, or 4% TCA solution, which had been cooled with ice in advance, was added in a volume of 1/4 with respect to each solution, mixed and kept on ice for 15 minutes. Then, each solution was divided in half. One part continued to be kept on ice. The other part was centrifuged with a compact refrigerated centrifuge at 10,000 r.p.m. at 4° C. for minutes to collect the supernatant.

A 2 M Tris solution, which had been cooled with ice in advance, was added to each solution to adjust to a pH of 8.0. It should be noted that the volume of 2 M Tris required for the adjustment to a pH of 8.0 was determined with the pilot study.

20 µL each of the solution after the neutralization were collected, diluted by adding 180 µL of purified water for the sample having the concentration of actinase at the test onset of 2% and 580 µL of purified water for the sample having the concentration of actinase at the test onset of 6%, respectively, kept on ice to use as the test sample for the measurement of the remaining protease activity.

As a standard for protease activity measurement, Actinase AF powder was dissolved in purified water to prepare 6% solution. The solution was used to prepare dilution series of 12.5 to 500 µg/mL as standard solutions.

50 µL each of the test sample and standard solution as described above was collected, added with 250 µL of a solution of 1.25% casein sodium (Wako Pure Chemical Industries, Ltd.), and reacted at 55° C. for 30 minutes. After that, 250 µL of 110 mM TCA were added to precipitate a protein, and centrifuged at 10,000×g for 10 minutes to collect 60 µL of the supernatant. The solution was added with 150 µL of a 500 mM sodium carbonate solution, and further added with 30 µL of a phenol reagent (Wako Pure Chemical Industries, Ltd.) diluted by a factor of four. Following the stirring and mixing, the resultant was reacted at 37° C. for 30 minutes and then the absorbance at a wavelength of 630 nm was measured.

The calibration curve was prepared with the concentration and absorbance of the standard solution. The remaining protease activity in the test sample was calculated as the concentration equivalent for the standard Actinase AF with the calibration curve and evaluated.

The results were shown in Table 36. For both the solution having concentration of actinase of 2% and the solution having concentration of actinase of 6%, the inventor confirmed that, when a method was performed in which the TCA treatment was conducted at concentrations of 8% and 2.4%, and the precipitate was removed with the centrifugation, followed by the neutralization of the supernatant, the remaining protease activity was able to be deactivated almost completely.

TABLE 36

Confirmation for protease deactivation in pretreatment operation

| Actinase Concentration | TCA treatment Concentration | Temperature | Time | Precipitation removal treatment | Neutralization treatment | Remaining activity (mg/mL equivalent) | Remaining activity (%) |
|---|---|---|---|---|---|---|---|
| 6% (60 mg/mL) | 8.00% | 0° C. | 15 | None | 2 M Tris | <0.9 | Less than 1.5% |
|  | 2.40% |  |  |  |  | <0.9 | Less than 1.5% |
|  | 0.80% |  |  |  |  | <0.9 | Less than 1.5% |
| 2% (20 mg/mL) | 8.00% |  |  |  |  | <0.3 | Less than 1.5% |
|  | 2.40% |  |  |  |  | <0.3 | Less than 1.5% |
|  | 0.80% |  |  |  |  | <0.3 | Less than 1.5% |
| 6% (60 mg/mL) | 8.00% |  |  | Centrifugation (at 4° C. for 5 minutes) |  | <0.9 | Less than 1.5% |
|  | 2.40% |  |  |  |  | <0.9 | Less than 1.5% |
|  | 0.80% |  |  |  |  | <0.9 | Less than 1.5% |
| 2% (20 mg/mL) | 8.00% |  |  |  |  | <0.3 | Less than 1.5% |
|  | 2.40% |  |  |  |  | <0.3 | Less than 1.5% |
|  | 0.80% |  |  |  |  | <0.3 | Less than 1.5% |

Example 19

Evaluation for Degree of the Molecular Weight Maintenance of HA in the Case of Performing Pretreatment Steps 2) and 3)

As the buffer for sample, 0.135 M NaCl-10 mM Tris-HCl (having a pH of 8.0) was prepared. The resultant was added with HA's having 3 kinds of molecular weights (HA-MW-STD-1, -2, and -3 in Table 1 in Example 1) so as to be a final concentration of 5 µg/mL to give a test sample.

Each of the test samples was dispensed into 3 tubes in a volume of 6 mL each and cooled with ice. To this, 1.5 mL of TCA solutions having 3 different concentrations (A: 40%, B: 12%, and C: 4%), which had been cooled with ice in advance, were added, mixed, kept on ice for 15 minutes, and then centrifuged at 3,000 r.p.m. using a refrigerated centrifuge at 4° C. for 5 minutes to collect 9.6 mL of the supernatant.

To each of the above solutions, an ice-cold 2 M Tris solution was added in an amount of 2.50 mL for A, 0.75 mL for B, and 0.27 mL for C to adjust the pH to 8.0. Subsequently, ice-cold purified water was added in an amount of 0 mL for A, 1.75 mL for B, 2.24 mL for C to achieve the same final volumes. 9.6 mL each of those solutions were collected, desalted with a PD-10 column (GE Healthcare Bio-Sciences KK) and then concentrated to dryness using a centrifugal evaporator without heating. For redissolution, 380 µL of 0.2 M NaCl were added.

With respect to the solution, GPC analysis was performed with a method in the same manner as that in Example 1 to measure the molecular weight of HA. The molecular weight of HA after the pretreatment as described above were compared with the molecular weight of the untreated HA to evaluate the degree of the molecular weight maintenance of HA in the pretreatment step.

The results were shown in Table 37. In the case where TCA was treated with a final concentration of 8%, each of HA-MWSTD-1 (molecular weight: 2,310 kDa), HA-MWSTD-2 (molecular weight: 1,410 kDa), and HA-MWSTD-03 (molecular weight: 993 kDa) samples had a degree of the molecular weight maintenance of 100%, 96%, and 103% which was evaluated at a peak molecular weight, respectively. In the case where TCA was treated with a final concentration of 2.4%, HA molecular weight each of HA-MWSTD-1, HA-MWSTD-2, and HA-MWSTD-3 samples had a degree of the molecular weight maintenance of 101%, 99%, and 102% which was evaluated at a peak molecular weight, respectively. In the case where TCA was treated with a final concentration of 0.8%, each of HA-MWSTD-1, HA-MWSTD-2, and HA-MWSTD-3 samples had a degree of the molecular weight maintenance of 97%, 95%, and 104% which was evaluated at a peak molecular weight, respectively.

TABLE 37

Validation 1 for degree of the molecular weight maintenance of hyaluronic acid in pretreatment operation

| Test sample | Molecular weight (kDa) | TCA treatment | | | Precipitation removal treatment | Neutralization treatment | GPC measurements (kDa) | degree of the molecular weight maintenance |
| --- | --- | --- | --- | --- | --- | --- | --- | --- |
| | | Concentration | Temperature | Time | | | | |
| HA-MWSTD-1 | 2,310 | Without treatment | | | | | 1,926 | |
| | | 8.00% | 0° C. | 15 | Centrifugation (4° C.) | 2 M Tris | 1,925 | 100% |
| | | 2.40% | 0° C. | 15 | Centrifugation (4° C.) | 2 M Tris | 1,954 | 101% |
| | | 0.80% | 0° C. | 15 | Centrifugation (4° C.) | 2 M Tris | 1,875 | 97% |
| HA-MWSTD-1 | 1,410 | Without treatment | | | | | 1,555 | |
| | | 8.00% | 0° C. | 15 | Centrifugation (4° C.) | 2 M Tris | 1,489 | 96% |
| | | 2.40% | 0° C. | 15 | Centrifugation (4° C.) | 2 M Tris | 1,533 | 99% |
| | | 0.80% | 0° C. | 15 | Centrifugation (4° C.) | 2 M Tris | 1,471 | 95% |
| HA-MWSTD-1 | 993 | Without treatment | | | | | 1,083 | |
| | | 8.00% | 0° C. | 15 | Centrifugation (4° C.) | 2 M Tris | 1,113 | 103% |
| | | 2.40% | 0° C. | 15 | Centrifugation (4° C.) | 2 M Tris | 1,101 | 102% |
| | | 0.80% | 0° C. | 15 | Centrifugation (4° C.) | 2 M Tris | 1,129 | 104% |

Example 20

Evaluation for Degree of the Molecular Weight Maintenance of HA in Case of Performing Pretreatment Steps 1), 2) and 3)

As the buffer for sample, 0.135 M NaCl-10 mM Tris-HCl (having a pH of 8.0) was prepared. To this, Actinase AF was dissolved to prepare solutions having concentrations of 6% (A) and 2% (B). In addition, a buffer for sample containing no actinase was prepared. Each of the above solution was added with HA's having 3 kinds of molecular weights (HA-MWSTD-1, -2, and -3 in Table 1 in Example 1) so as to be a final concentration of 5 µg/mL to give a test sample.

Each of the test samples was treated in a hot-water bath at 37° C. for 24 hours, and collected in a volume of 6 mL each and cooled with ice. To this, 1.5 mL of 40% TCA solutions, which had been cooled with ice in advance, were added, mixed, kept on ice for 15 minutes, and then centrifuged at 3,000 r.p.m. using a refrigerated centrifuge at 4° C. for 5 minutes to collect 9.6 mL of the supernatant.

To each of the above solutions, an ice-cold 2 M Tris solution was added in an amount of 2.65 mL to adjust to the pH of 8.0. Each of the solutions after adjustment was collected, desalted with a PD-10 column (GE Healthcare Bio-Sciences KK) and then concentrated to dryness using a centrifugal evaporator without heating. For redissolution, 380 μL of 0.2 M NaCl were added.

With respect to the solution, GPC analysis was performed with a method in the same manner as that in Example 1 to measure the molecular weight of HA. The molecular weight of HA after the pretreatment as described above was compared with the molecular weight of the untreated HA to evaluate the degree of the molecular weight maintenance of HA in the pretreatment step.

The results were shown in Table 38. In the case of the treatment at a 2% actinase concentration at 37° C. for 24 hours, each of HA-MWSTD-1 (molecular weight: 2,310 kDa), HA-MWSTD-2 (molecular weight: 1,410 kDa), and HA-MWSTD-3 (molecular weight: 993 kDa) samples had a degree of the molecular weight maintenance of 89%, 91%, and 96% which was evaluated at a peak molecular weight, respectively. In the case of the treatment at 6% actinase concentration at 42° C. for 24 hours, each of HA-MWSTD-1, HA-MWSTD-2, and HA-MWSTD-3 samples had a degree of the molecular weight maintenance of 74%, 80%, and 89% which was evaluated at a peak molecular weight, respectively.

200, 100, 50, 25, and 12.5 ng/mL with respect to HA's having 4 kinds of molecular weights (samples B, E, H, and J in Table 1 in Example 1). The measurement step (1) was performed with a method in the same manner as that in Example 3.

Figure 18:
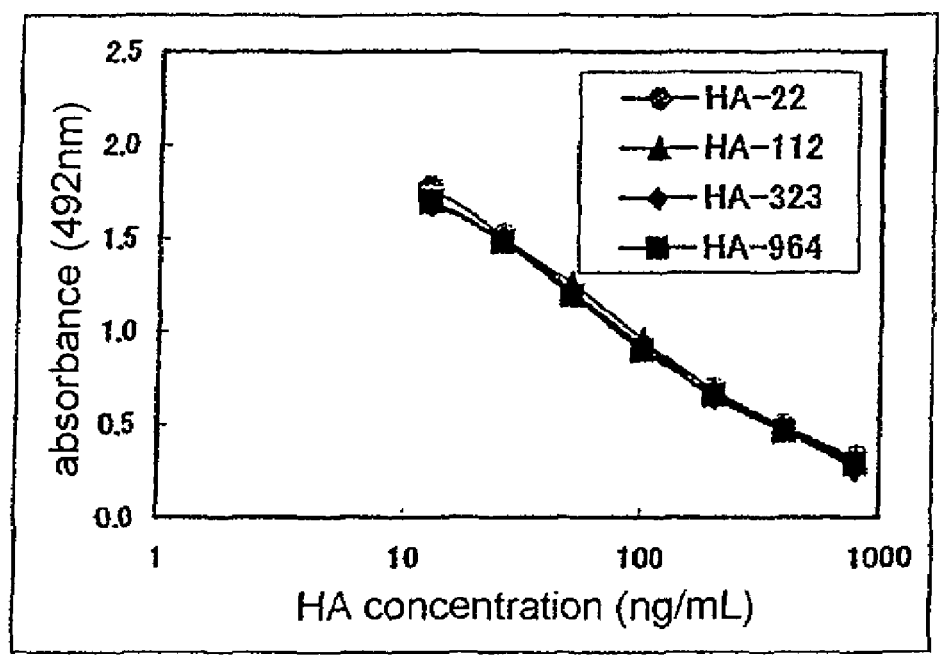
FIG. 18 is a graph showing results of tests for confirming that pretreatment reagents do not affect a measurement step (1).

The measurement results and the graph with the results being plotted were shown in Table 40 and FIG. 18, respectively. The inventor confirmed that, in the case where the any of the simulated treatment solutions A, B, and C was used, the same reactivity was exhibited independently of the molecular weight of HA. The inventor confirmed that, even if the test sample solution still contained reagents for protease deactivation and reagents for neutralization added in the pretreatment step, the solvent for the standard adjusted to the same composition as the solvent for the test sample was able to be used to perform the measurement step (1).

TABLE 39

|  |  | A | B | C |
|---|---|---|---|---|
| Buffer for test sample | Collection amount (mL) | 6 | 6 | 6 |
|  | Tris concentration (M) | 0.01 | 0.01 | 0.01 |
|  | NaCl concentration (M) | 0.135 | 0.135 | 0.135 |
| Solution for protein removal | Addition amount (mL) | 1.5 | 1.5 | 1.5 |
|  | TCA concentration (%) | 40% | 12% | 4% |
| Solution for neutralization | Addition amount (mL) | 2.5 | 0.75 | 0.25 |
|  | Tris concentration (M) | 2 | 2 | 2 |
| Purified water for volume correction | Addition amount (mL) | 0 | 1.75 | 2.25 |

TABLE 38

Validation 2 for degree of the molecular weight maintenance of hyaluronic acid in pretreatment operation

| Test sample | Molecular weight (kDa) | Actinase treatment | | | TCA treatment | | | Precipitation removal treatment | Neutralization treatment | GPC measurements (kDa) | degree of the molecular weight maintenance |
|---|---|---|---|---|---|---|---|---|---|---|---|
|  |  | Concentration | Temperature | Time | Concentration | Temperature | Time |  |  |  |  |
| HA-MWSTD-1 | 2,310 |  |  |  | Without treatment | | | | | 1,926 |  |
|  |  | 2.00% | 37° C. | 24 | 8.00% | 0° C. | 15 | Centrifugation (4° C.) | 2 M Tris | 1,715 | 89% |
| HA-MWSTD-2 | 1,410 |  |  |  | Without treatment | | | | | 1,555 |  |
|  |  | 2.00% | 37° C. | 24 | 8.00% | 0° C. | 15 | Centrifugation (4° C.) | 2 M Tris | 1,417 | 91% |
| HA-MWSTD-3 | 993 |  |  |  | Without treatment | | | | | 1,083 |  |
|  |  | 2.00% | 37° C. | 24 | 8.00% | 0° C. | 15 | Centrifugation (4° C.) | 2 M Tris | 1,036 | 96% |
| HA-MWSTD-1 | 2,310 |  |  |  | Without treatment | | | | | 1,988 |  |
|  |  | 6.00% | 42° C. | 24 | 8.00% | 0° C. | 15 | Centrifugation (4° C.) | 2 M Tris | 1,468 | 74% |
| HA-MWSTD-2 | 1,410 |  |  |  | Without treatment | | | | | 1,507 |  |
|  |  | 6.00% | 42° C. | 24 | 8.00% | 0° C. | 15 | Centrifugation (4° C.) | 2 M Tris | 1,212 | 80% |
| HA-MWSTD-3 | 993 |  |  |  | Without treatment | | | | | 1,079 |  |
|  |  | 6.00% | 42° C. | 24 | 8.00% | 0° C. | 15 | Centrifugation (4° C.) | 2 M Tris | 959 | 89% |

Example 21

Confirmation for Influence of Solvent Composition After Implementation of Pretreatment Steps 2), 3), and 4) on Measurement Step (1)

TCA solutions having 3 different concentrations, 2 M Tris solutions, correction solutions for ELISA, and D.W. were mixed at a proportion in Table 39 to prepare simulated pretreatment solutions A, B, and C. The treatment solutions were used to prepare dilution series of concentrations of 800, 400, TABLE 39-continued

|  |  | A | B | C |
|---|---|---|---|---|
| Composition after neutralization | Solution volume | 10 | 10 | 10 |
|  | TCA concentration (%) | 6.00% | 1.80% | 0.60% |
|  | Tris concentration (M) | 0.5 | 0.15 | 0.05 |
|  | NaCl concentration (M) | 0.081 | 0.081 | 0.081 |
| Sample solution after neutralization | Collection amount (mL) | 8 | 8 | 8 |

TABLE 39-continued

|  |  | A | B | C |
|---|---|---|---|---|
| Solution for correction | Addition amount (mL) | 12 | 2 | 2 |
|  | Tris concentration (M) | 0 | 0.4 | 0.8 |
|  | NaCl concentration (M) | 0.171 | 0.351 | 0.351 |
|  | BSA concentration (%) | 1.67 | 5 | 5 |
| Composition after correction | TCA concentration (%) | 2.40% | 1.44% | 0.48% |
|  | Tris concentration (M) | 0.2 | 0.2 | 0.2 |
|  | NaCl concentration (M) | 0.135 | 0.135 | 0.135 |
|  | BSA concentration (M) | 1 | 1 | 1 |

TABLE 40

Confirmation for influence of composition of pretreatment solution on measurement step 1

| | Sample | | | |
|---|---|---|---|---|
| | J | H | E | B |
| | | HA molecular weight (kDa) | | |
| HA concentration (ng/mL) | 22 | 112 | 323 | 964 |
| | Absorbance (492 nm) | | | |
| 0 | 2.085 | 1.937 | 1.889 | 2.081 |
| 12.5 | 1.769 | 1.703 | 1.675 | 1.692 |
| 25 | 1.516 | 1.493 | 1.501 | 1.482 |
| 50 | 1.215 | 1.256 | 1.195 | 1.193 |
| 100 | 0.926 | 0.958 | 0.922 | 0.898 |
| 200 | 0.684 | 0.681 | 0.642 | 0.654 |
| 400 | 0.489 | 0.473 | 0.461 | 0.461 |
| 800 | 0.321 | 0.3 | 0.257 | 0.287 |

Example 22

Confirmation for Influence of Solvent Composition after the Pretreatment Steps 2), 3), and 4) being Performed on Measurement Step (2)

For HA's having 4 kinds of molecular weights (samples B, E, H, and J in Example 1, Table 1), the simulated pretreatment solution A, B, and C prepared in Example 21 was used to prepare dilution series having concentrations of 1,000, 300, 100, and 30 ng/mL. Those were reacted and measured in the same manner as that in Example 5 except for the following conditions.

HABP immobilization concentration: 30 and 100 ng/mL

Buffer at the time of the HABP immobilization: PBS

HABP immobilization plate: A dry plate prepared with 3 kinds of blocking agents was used.

Buffer in which HA standard is dissolved: ELISA basic buffer

Biotin-HABP concentration: 200 ng/mL

Figure 19:
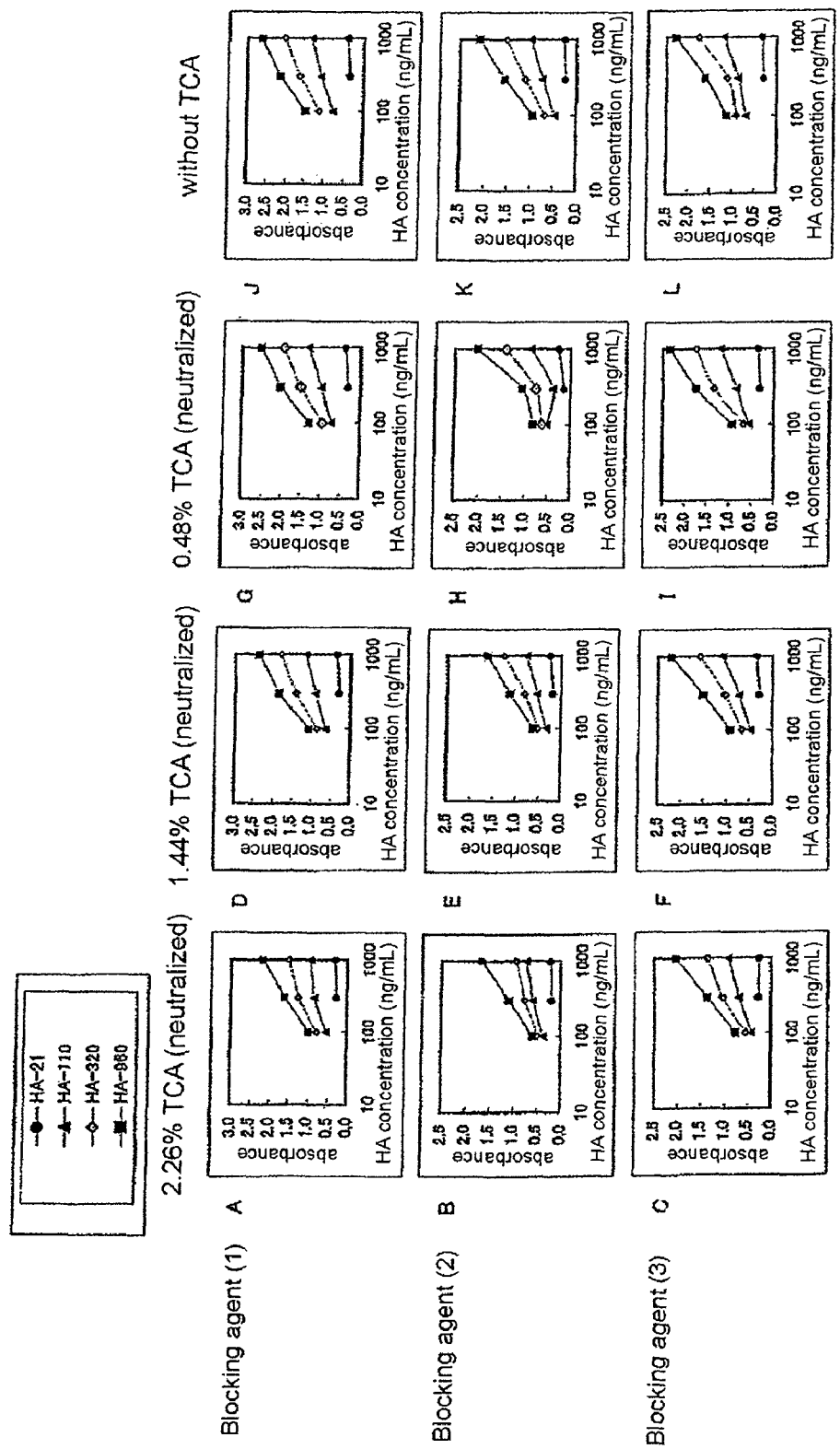
FIG. 19 are graphs each showing results of tests for confirming that pretreatment reagents do not affect a measurement step (2).
Figure 20:
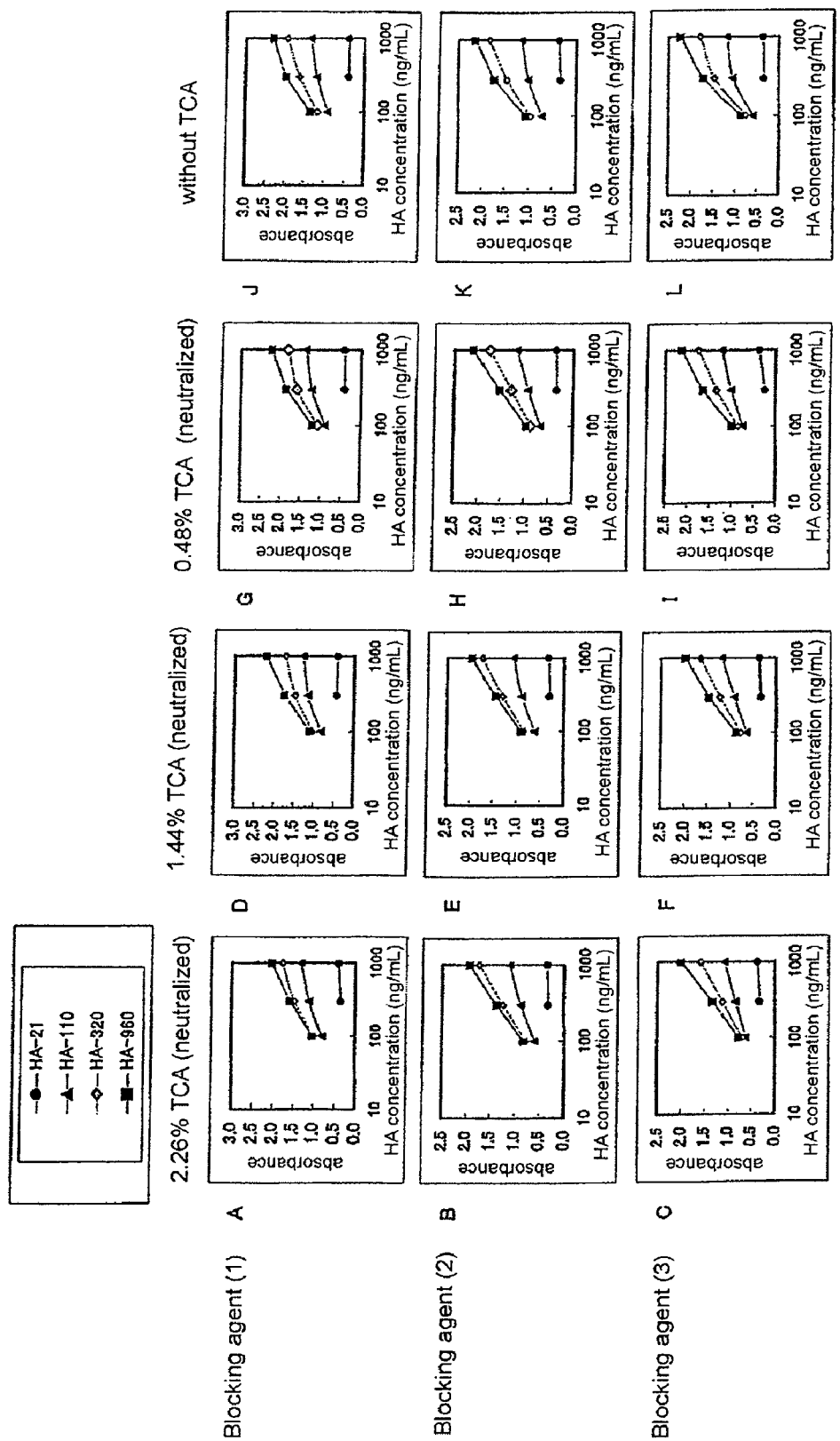
FIG. 20 are graphs each showing results of tests for confirming that pretreatment reagents do not affect the measurement step (2).

Addition concentration of guanidine hydrochloride to biotin-HABP solution: 0.4 and 0.8 M HRP-avidin concentration: 500 ng/mL Kind and concentration of coloring solution: OPD: 0.5 mg/mL The reaction condition at HABP immobilization concentration of 30 ng/mL, the results, and the ratio between the absorbances obtained from each sample calculated from the results were shown in Table 41, FIG. 19, and Table 42, respectively. Further, the reaction condition at HABP immobilization concentration of 100 ng/mL, the results, and the ratio between the absorbances obtained from each sample calculated from the results were shown in Table 43, FIG. 20, and Table 44, respectively.

In any case where the simulated treatment solutions A, B, and C were used, the inventor confirmed that the reaction intensity in proportion to the molecular weight of HA was shown. From the foregoing, even if the test sample solution still contained reagents for protease deactivation and reagents for neutralization added in the pretreatment step, the solvent for the standard adjusted to the same composition as the solvent for the test sample was able to be used to perform the measurement step (2).

TABLE 41

| | Reaction condition | | | | | | | | | | | |
|---|---|---|---|---|---|---|---|---|---|---|---|---|
| Performance condition | A | B | C | D | E | F | G | H | I | J | K | L |
| Concentration of TCA contained in HA standard solution | 2.26% | | | 1.44% | | | 0.48% | | | 0% | | |
| HABP immobilization concentration (ng/mL) | 30 | 30 | 30 | 30 | 30 | 30 | 30 | 30 | 30 | 30 | 30 | 30 |
| Blocking agent for HABP immobilization plate | (1) | (2) | (3) | (1) | (2) | (3) | (1) | (2) | (3) | (1) | (2) | (3) |
| Biotin-HABP concentration (ng/mL) | 200 | 200 | 200 | 200 | 200 | 200 | 200 | 200 | 200 | 200 | 200 | 200 |
| Concentration of guanidine hydrochloride added to HA standard solution (M) | 0 | 0 | 0 | 0 | 0 | 0 | 0 | 0 | 0 | 0 | 0 | 0 |
| Concentration of guanidine hydrochloride added to biotin-HABP solution (M) | 0.4 | 0.4 | 0.4 | 0.4 | 0.4 | 0.4 | 0.4 | 0.4 | 0.4 | 0.4 | 0.4 | 0.4 |
| HRP-avidin concentration (ng/mL) | 500 | 500 | 500 | 500 | 500 | 500 | 500 | 500 | 500 | 500 | 500 | 500 |
| Coloring substrate | OPD | OPD | OPD | OPD | OPD | OPD | OPD | OPD | OPD | OPD | OPD | OPD |
| Coloring substrate concentration (mg/mL) | 0.5 | 0.5 | 0.5 | 0.5 | 0.5 | 0.5 | 0.5 | 0.5 | 0.5 | 0.5 | 0.5 | 0.5 |

Blocking agent for HABP immobilization plate:
(1) Applie Block;
(2) 1% BSA-2% sucrose; and
(3) Immunoassay stabilizer

TABLE 42

Reaction proportion of HA's having various molecular weights

|  | A | B | C | D | E | F | G | H | I | J | K | L |
|---|---|---|---|---|---|---|---|---|---|---|---|---|
| Absorbance of blank | 0.189 | 0.115 | 0.146 | 0.185 | 0.115 | 0.141 | 0.189 | 0.113 | 0.14 | 0.107 | 0.061 | 0 |
| Absorbance ratio of HA-21 to HA-960 (HA concentration of 100 ng/mL) | 0% | 0% | 0% | 0% | 0% | 0% | 0% | 0% | 0% | 0% | 0% | 0% |
| Absorbance ratio of HA-110 to HA-960 (HA concentration of 100 ng/mL) | 44% | 52% | 43% | 51% | 42% | 43% | 48% | 55% | 51% | 48% | 46% | 60% |
| Absorbance ratio of HA-320 to HA-960 (HA concentration of 100 ng/mL) | 73% | 75% | 63% | 76% | 78% | 65% | 68% | 72% | 65% | 74% | 71% | 80% |
| Absorbance ratio of HA-21 to HA-960 (HA concentration of 300 ng/mL) | 6% | 7% | 9% | 7% | 7% | 10% | 7% | 4% | 11% | 8% | 14% | 9% |
| Absorbance ratio of HA-110 to HA-960 (HA concentration of 300 ng/mL) | 45% | 47% | 43% | 41% | 41% | 42% | 43% | 28% | 44% | 47% | 45% | 54% |
| Absorbance ratio of HA-320 to HA-960 (HA concentration of 300 ng/mL) | 74% | 65% | 72% | 72% | 68% | 65% | 71% | 69% | 75% | 74% | 70% | 69% |
| Absorbance ratio of HA-21 to HA-960 (HA concentration of 1,000 ng/mL) | 6% | 6% | 5% | 7% | 8% | 10% | 8% | 8% | 9% | 9% | 8% | 8% |
| Absorbance ratio of HA-110 to HA-960 (HA concentration of 1,000 ng/mL) | 37% | 40% | 40% | 44% | 43% | 46% | 47% | 39% | 48% | 48% | 45% | 54% |
| Absorbance ratio of HA-320 to HA-960 (HA concentration of 1,000 ng/mL) | 66% | 54% | 64% | 74% | 76% | 69% | 75% | 67% | 73% | 76% | 71% | 77% |

* Calculation was made with a value obtained by subtracting the absorbance of the blank.

TABLE 43

Reaction condition

| Performance condition | A | B | C | D | E | F | G | H | I | J | K | L |
|---|---|---|---|---|---|---|---|---|---|---|---|---|
| Concentration of TCA contained in HA standard solution | 2.26% |  |  | 1.44% |  |  | 0.48% |  |  | 0% |  |  |
| HABP immobilization concentration (ng/mL) | 30 | 30 | 30 | 30 | 30 | 30 | 30 | 30 | 30 | 30 | 30 | 30 |
| Blocking agent for HABP immobilization plate | (1) | (2) | (3) | (1) | (2) | (3) | (1) | (2) | (3) | (1) | (2) | (3) |
| Biotin-HABP concentration (ng/mL) | 200 | 200 | 200 | 200 | 200 | 200 | 200 | 200 | 200 | 200 | 200 | 200 |
| Concentration of guanidine hydrochloride added to HA standard solution (M) | 0 | 0 | 0 | 0 | 0 | 0 | 0 | 0 | 0 | 0 | 0 | 0 |
| Concentration of guanidine hydrochloride added to biotin-HABP solution (M) | 0.8 | 0.8 | 0.8 | 0.8 | 0.8 | 0.8 | 0.8 | 0.8 | 0.8 | 0.8 | 0.8 | 0.8 |
| HRP-avidin concentration (ng/mL) | 500 | 500 | 500 | 500 | 500 | 500 | 500 | 500 | 500 | 500 | 500 | 500 |
| Coloring substrate | OPD | OPD | OPD | OPD | OPD | OPD | OPD | OPD | OPD | OPD | OPD | OPD |
| Coloring substrate concentration (mg/mL) | 0.5 | 0.5 | 0.5 | 0.5 | 0.5 | 0.5 | 0.5 | 0.5 | 0.5 | 0.5 | 0.5 | 0.5 |

Blocking agent for HABP immobilization plate:
(1) Applie Block;
(2) 1% BSA-2% sucrose; and
(3) Immunoassay stabilizer

TABLE 44

Reaction proportion of HA's having various molecular weights

|  | A | B | C | D | E | F | G | H | I | J | K | L |
|---|---|---|---|---|---|---|---|---|---|---|---|---|
| Absorbance of blank | 0.275 | 0.206 | 0.21 | 0.244 | 0.185 | 0.198 | 0.229 | 0.167 | 0.238 | 0.113 | 0.093 | 0.068 |
| Absorbance ratio of HA-21 to HA-960 (HA concentration of 100 ng/mL) | 0% | 0% | 0% | 0% | 0% | 0% | 0% | 0% | 0% | 0% | 0% | 0% |
| Absorbance ratio of HA-110 to HA-960 (HA concentration of 100 ng/mL) | 71% | 62% | 72% | 67% | 60% | 65% | 68% | 63% | 67% | 65% | 64% | 65% |
| Absorbance ratio of HA-320 to HA-960 (HA concentration of 100 ng/mL) | 95% | 92% | 87% | 92% | 91% | 84% | 87% | 88% | 81% | 85% | 89% | 85% |
| Absorbance ratio of HA-21 to HA-960 (HA concentration of 300 ng/mL) | 7% | 10% | 10% | 12% | 9% | 10% | 11% | 13% | 1% | 10% | 12% | 7% |
| Absorbance ratio of HA-110 to HA-960 (HA concentration of 300 ng/mL) | 65% | 58% | 56% | 61% | 56% | 57% | 60% | 56% | 55% | 58% | 56% | 60% |
| Absorbance ratio of HA-320 to HA-960 (HA concentration of 300 ng/mL) | 92% | 89% | 80% | 82% | 88% | 81% | 83% | 83% | 79% | 81% | 83% | 85% |

TABLE 44-continued

| Reaction proportion of HA's having various molecular weights | | | | | | | | | | | | |
|---|---|---|---|---|---|---|---|---|---|---|---|---|
| | A | B | C | D | E | F | G | H | I | J | K | L |
| Absorbance ratio of HA-21 to HA-960 (HA concentration of 1,000 ng/mL) | 8% | 8% | 8% | 9% | 8% | 10% | 9% | 9% | 7% | 8% | 11% | 7% |
| Absorbance ratio of HA-110 to HA-960 (HA concentration of 1,000 ng/mL) | 59% | 52% | 49% | 52% | 50% | 56% | 56% | 51% | 52% | 56% | 52% | 60% |
| Absorbance ratio of HA-320 to HA-960 (HA concentration of 1,000 ng/mL) | 84% | 88% | 77% | 74% | 87% | 82% | 78% | 81% | 79% | 83% | 85% | 80% |

*Calculation was made with a value obtained by subtracting the absorbance of the blank.

Example 23

Measurement Results of HA Concentration in Various Biotic Samples in the Case of Applying Condition Settled on Basis of Results from Examples 18 to 22 (HPLC Method)

Actinase AF was dissolved in 10 mM Tris-HCl (pH 8.0) to prepare a 2% solution and 4 mL of the resultant was added to 400 mg of porcine cartilage tissue sample to give a test sample 1.

Similarly, Actinase AF was dissolved in 10 mM Tris-HCl (pH 8.0) to prepare 10% solution, and 1 mL of the resultant was added to 4 mL of culture supernatant of human synovial membrane cell line to give a test sample 2.

Each of the test samples was treated in a warm bath at 37° C. for 24 hours. After that, 3 mL of the resultant was collected and cooled with ice, following which 0.75 mL of a 40% TCA solution, which had been cooled with ice in advance, was added and mixed. The resultant was kept on ice for 15 minutes and then centrifuged using a refrigerated centrifuge at 3,000 r.p.m. at 4° C. for 5 minutes to collect 4.8 mL of the supernatant.

Each of the solutions as described above was added with 1.33 mL of ice-cold 2 M Tris solution to adjust the pH to 8.0. Each of the solutions after the adjustment was desalted with a PD-10 column (GE Healthcare Bio-Sciences KK) and then evaporated to dryness using a centrifugal evaporator without heating, following which 0.2 M NaCl was added to redissolve.

With respect to the solution, HPLC analysis was performed with a method in the same manner as that in Example 2 to measure the concentration of HA.

The results were shown in Table 45.

Example 24

Measurement Results of HA Molecular Weight in Various Biotic Samples in the Case of Applying Condition Settled on Basis of Results from Examples 18 to 22 (GPC Method)

With respect to the redissolved solution after the desalting and concentration obtained in Example 23, GPC analysis was performed with a method in the same manner as that in Example 1 to determine the molecular weight of HA.

The results were shown in Table 45.

Example 25

Measurement Results of HA Concentration in Various Biotic Samples in the Case of Applying Condition Settled on Basis of Results from Examples 18 to 22 (ELISA Method (Measurement Step (1))

30 μL of 2 M solution of each specimen in Tris obtained in Example 23 were collected and added with 48.3 μL of the correction solution for ELISA shown in Example 21 to prepare a test sample solution. A standard for concentration of HA was prepared with a method in the same manner as that in Example 21.

The above standard solution and test sample solution were measured with a method in the same manner as that in Example 16 to measure the concentration of HA.

The results were shown in Table 45. Good consistency was obtained between measurements with the present method and values with HPLC method obtained in Example 23.

TABLE 45

| Measurements for biotic sample - concordance rate to HPLC method and GPC method - | | | | | | |
|---|---|---|---|---|---|---|
| | | | Measurement step 1 | Measurement step 2, 3 | | |
| Method for analysis Specimen | HPLC HA concentration measurements (ng/mL) | GPC Molecular weight measurements (kDa) | HA concentration measurements (ng/mL) | Concordance rate to HPLC method (%) | Molecular weight measurements (kDa) | Concordance rate to GPC method (%) |
| Porcine cartilage | 5.27 | 295 | 6.4 | 121% | 224 | 76% |
| Culture supernatant of human synovial cell line | 0.74 | 395 | 0.9 | 122% | 366 | 93% |

Example 26

Measurement Results of HA Molecular Weight in Various Biotic Samples in the Case of Applying Condition Settled on Basis of Results from Examples 18 to 22 (ELISA Method (Measurement Step (2), (3))

Each of the test sample solutions prepared in Example 25 was dissolved with the simulated pretreatment solution A prepared in Example 21 based on the results from Example 25. The HA concentration of the resultant was adjusted to 100 ng/mL, to thereby obtain a test sample. A standard for the molecular weight of HA was prepared with a method in the same manner as that in Example 21.

The above standard solution and test sample were measured with a method in the same manner as that in Example 16 to measure the molecular weight of HA.

The results were shown in Table 45. Good consistency was obtained between measurements with the present method and values with GPC method obtained in Example 24.

What is claimed is:

1. A method of measuring a molecular weight of hyaluronic acid, comprising at least the following steps (1) to (3):
    (1) measuring a concentration of hyaluronic acid in a sample;
    (2) reacting hyaluronic acid in a sample containing the hyaluronic acid with a hyaluronic acid-binding protein, and measuring an amount of the hyaluronic acid-binding protein that is bound to the hyaluronic acid in the sample or a value that reflects the amount; and
    (3) determining the molecular weight of the hyaluronic acid in the sample from the concentration of the hyaluronic acid in the sample obtained in step (1); and the amount of the hyaluronic acid-binding protein that is bound to the hyaluronic acid in the sample or the value that reflects the amount obtained in step (2),
        wherein the molecular weight in the sample is determined from a relationship between the molecular weight in a standard hyaluronic acid sample with known concentration and molecular weight and the amount of the hyaluronic acid-binding protein binding to the standard hyaluronic acid sample or the value that reflects the amount.

2. The method according to claim 1, wherein step (2) comprises the following steps (i) to (iv):
    (i) immobilizing the hyaluronic acid-binding protein to a solid phase;
    (ii) reacting the hyaluronic acid-binding protein that is immobilized to the solid phase with the hyaluronic acid in a sample;
    (iii) further reacting the hyaluronic acid that is bound to the hyaluronic acid-binding protein that is immobilized to the solid phase with a labeled hyaluronic acid-binding protein; and
    (iv) measuring an amount of the labeled hyaluronic acid-binding protein that is bound to the hyaluronic acid in step (iii) or a value that reflects the amount.

3. The method according to claim 2, wherein a label substance of the labeled hyaluronic acid-binding protein to be used in step (iii) is selected from the group consisting of biotin, avidin, an enzyme, an isotope, a fluorescent pigment, and a chemiluminescent substance.

4. The method according to claim 2, wherein a label substance of the labeled hyaluronic acid-binding protein to be used in the step (iii) is biotin or avidin.

5. The method according to claim 1, wherein the relationship between the molecular weight of the hyaluronic acid and the amount of the hyaluronic acid-binding protein binding to the hyaluronic acid or the value that reflects the amount, the relationship being used in step (3) and obtained from the standard hyaluronic acid sample with known concentration and molecular weight, is represented by a standard curve that is obtained by performing step (2) using the hyaluronic acid standard solution with known concentration and molecular weight as the sample.

6. The method according to claim 1, wherein, in step (3), the concentration of the hyaluronic acid in the sample that is obtained in step (1) is used as an index for dilution of the sample or used for calculation for the amount of the hyaluronic acid-binding protein binding to the hyaluronic acid in the standard hyaluronic acid sample at the concentration or the value that reflects the amount.

7. The method according to claim 2, wherein, in reacting the hyaluronic acid with the hyaluronic acid-binding protein, the amount of the hyaluronic acid-binding protein that is bound to the hyaluronic acid is adjusted by allowing an additive selected from a protein denaturant, an acidic polysaccharide, and a surfactant to coexist and regulating an amount of the additive.

8. The method according to claim 2, wherein the amount of the hyaluronic acid-binding protein that is bound to the hyaluronic acid or the value that reflects the amount to be measured in step (iv) is regulated by changing the amount of the hyaluronic acid to be immobilized in step (i) or the amount of the hyaluronic acid-binding protein to be reacted in step (iii).

9. The method according to claim 7, wherein the additive comprises guanidine hydrochloride.

10. The method according to claim 2, wherein the amount of the hyaluronic acid-binding protein to be immobilized is 3 to 30,000 ng/mL as the concentration of a solution of the hyaluronic acid-binding protein to be used for the immobilization.

11. The method according to claim 2, wherein:
    the labeled hyaluronic acid-binding protein to be reacted in step (iii) comprises a biotin-labeled hyaluronic acid-binding protein; and
    a solution of the biotin-labeled protein has a concentration of 10 to 30,000 ng/mL.

12. The method according to claim 9, wherein guanidine hydrochloride in the hyaluronic acid standard solution and/or the sample have/has a concentration up to 3.6 M at a final concentration.

13. The method according to claim 9, wherein guanidine hydrochloride in the solution of the biotin-labeled hyaluronic acid-binding protein has a concentration up to 1.6 M at a final concentration.

* * * * *

UNITED STATES PATENT AND TRADEMARK OFFICE
CERTIFICATE OF CORRECTION

| | | |
|---|---|---|
| PATENT NO. | : 8,163,498 B2 | Page 1 of 1 |
| APPLICATION NO. | : 12/376921 | |
| DATED | : April 24, 2012 | |
| INVENTOR(S) | : Hiroshi Fujita | |

Figure 12:
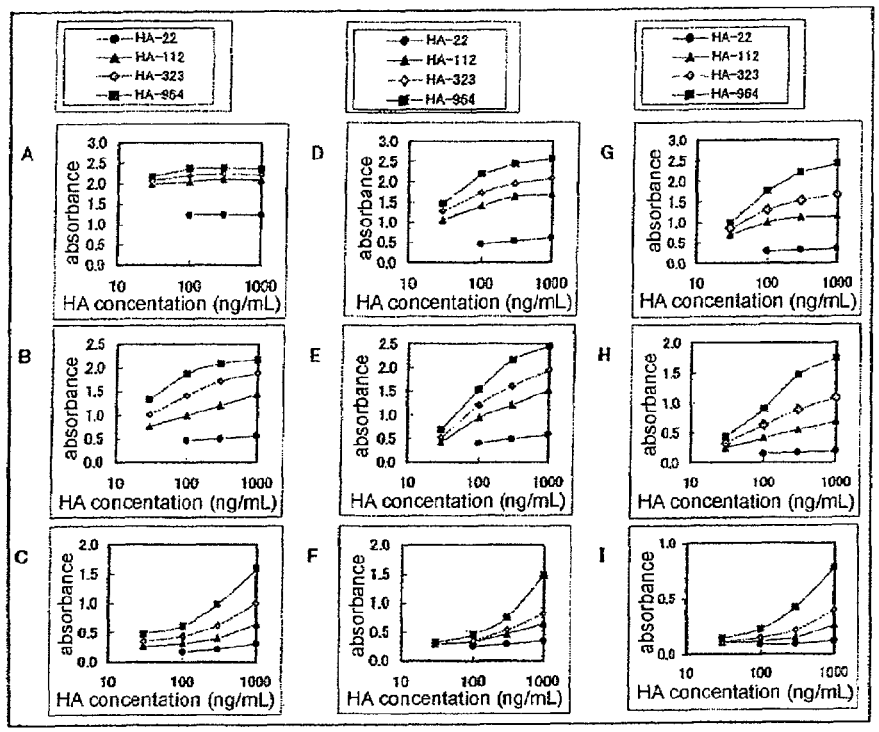
FIG. 12 are graphs showing results of tests for combination of various conditions.

It is certified that error appears in the above-identified patent and that said Letters Patent is hereby corrected as shown below:

Drawing Sheet 10 of 15, Fig. 12, Box A, Line 9, "concentation" should be changed to --concentration--

Drawing Sheet 10 of 15, Fig. 12, Box B, Line 8, "concentation" should be changed to --concentration--

Drawing Sheet 10 of 15, Fig. 12, Box C, Line 7, "concentation" should be changed to --concentration--

Drawing Sheet 10 of 15, Fig. 12, Box D, Line 9, "concentation" should be changed to --concentration--

Drawing Sheet 10 of 15, Fig. 12, Box E, Line 8, "concentation" should be changed to --concentration--

Drawing Sheet 10 of 15, Fig. 12, Box F, Line 7, "concentation" should be changed to --concentration--

Drawing Sheet 10 of 15, Fig. 12, Box G, Line 9, "concentation" should be changed to --concentration--

Drawing Sheet 10 of 15, Fig. 12, Box H, Line 8, "concentation" should be changed to --concentration--

Drawing Sheet 10 of 15, Fig. 12, Box I, Line 7, "concentation" should be changed to --concentration--

Column 1, Lines 33-34, "streptoavidin" should be changed to --streptavidin--

Column 13, Line 3, "(having 3or more" should be changed to --(having 3 or more--

Column 16, Line 44, "Co. LTd.)" should be changed to --Co. Ltd.)--

Column 47, Line 30, "for minutes to" should be changed to --for 5 minutes to--

Claim 10, Column 60, Line 42, "3to 30,000" should be changed to --3 to 30,000--

Signed and Sealed this
Eighteenth Day of September, 2012

David J. Kappos
*Director of the United States Patent and Trademark Office*